US011806245B2

(12) United States Patent
Spetzger

(10) Patent No.: US 11,806,245 B2
(45) Date of Patent: *Nov. 7, 2023

(54) EXPANDABLE INTERVERTEBRAL IMPLANT

(71) Applicant: EIT Emerging Implant Technologies GmbH, Wurmlingen (DE)

(72) Inventor: Uwe Spetzger, Wurmlingen (DE)

(73) Assignee: EIT Emerging Implant Technologies GmbH

( * ) Notice: Subject to any disclaimer, the term of this patent is extended or adjusted under 35 U.S.C. 154(b) by 0 days.

This patent is subject to a terminal disclaimer.

(21) Appl. No.: 17/822,639

(22) Filed: Aug. 26, 2022

(65) Prior Publication Data
US 2022/0409386 A1    Dec. 29, 2022

Related U.S. Application Data

(63) Continuation of application No. 16/842,058, filed on Apr. 7, 2020, now Pat. No. 11,426,286.

(60) Provisional application No. 62/986,156, filed on Mar. 6, 2020.

(51) Int. Cl.
*A61F 2/44*    (2006.01)

(52) U.S. Cl.
CPC ...... *A61F 2/442* (2013.01); *A61F 2002/4435* (2013.01); *A61F 2250/0007* (2013.01); *A61F 2250/0009* (2013.01)

(58) Field of Classification Search
CPC .............. A61F 2/442; A61F 2002/4435; A61F 2250/0007; A61F 2250/0008; A61F 2250/0009
See application file for complete search history.

(56) References Cited

U.S. PATENT DOCUMENTS

| 1,802,560 A | 4/1931 | Kerwin |
| 1,924,695 A | 8/1933 | Olson |
| 1,965,653 A | 7/1934 | Kennedy |
| 2,077,804 A | 4/1937 | Morrison |

(Continued)

FOREIGN PATENT DOCUMENTS

| AU | 2006279558 A1 | 2/2007 |
| AU | 2005314079 B2 | 7/2012 |

(Continued)

OTHER PUBLICATIONS

[No Author Listed] Porocoat® Porous Coating, Depuy Synthes Companies, 2015, 2 pages, webpage, accessed Jul. 5, 2016, <https://emea.depuysynthes.com/hcp/hip/products/qs/porocoat-porous-coating-emea>.

(Continued)

*Primary Examiner* — Kevin T Truong
*Assistant Examiner* — Diana Jones
(74) *Attorney, Agent, or Firm* — BakerHostetler

(57) ABSTRACT

An intervertebral implant is configured to be implanted in an intervertebral space in a first initial configuration. Subsequently, an actuator is configured to be driven in an actuation direction such that the actuator urges the implant to expand along a first expansion direction. Once the implant has been fully expanded along the first expansion direction, the actuator is configured to be further driven in the actuation direction so as to expand the implant in a second expansion direction that is perpendicular to the first expansion direction.

17 Claims, 7 Drawing Sheets

(56) References Cited

U.S. PATENT DOCUMENTS

| | | |
|---|---|---|
| 2,115,250 A | 4/1938 | Bruson |
| 2,121,193 A | 6/1938 | Hanicke |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Moreira |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 2,706,701 A | 4/1955 | Hans et al. |
| 2,710,277 A | 6/1955 | Shelanski et al. |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Johnson |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,175,555 A | 11/1979 | Herbert |
| 4,205,399 A | 6/1980 | Jamiolkowski et al. |
| 4,208,511 A | 6/1980 | Jamiolkowski et al. |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | McCarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,538,612 A | 9/1985 | Patrick, Jr. |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,646,741 A | 3/1987 | Smith |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,706,670 A | 11/1987 | Andersen et al. |
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Uther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,834,757 A | 5/1989 | Brantigan |
| 4,838,282 A | 6/1989 | Strasser et al. |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,889,119 A | 12/1989 | Jamiolkowski et al. |
| 4,892,550 A | 1/1990 | Huebsch |
| 4,896,662 A | 1/1990 | Noble |
| 4,898,186 A | 2/1990 | Kada et al. |
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |
| 4,940,467 A | 7/1990 | Tronzo |
| 4,941,466 A | 7/1990 | Romano |
| 4,946,378 A | 8/1990 | Hirayama et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Baumgart |

(56) References Cited

U.S. PATENT DOCUMENTS

| | | |
|---|---|---|
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Jeffrey |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Azarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muehling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |

(56) References Cited

U.S. PATENT DOCUMENTS

| | | |
|---|---|---|
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,556 A | 2/1997 | Pisharodi |
| 5,601,561 A | 2/1997 | Terry et al. |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Ower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Rrico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Arsen et al. |
| 5,782,865 A | 7/1998 | Grotz |
| 5,788,703 A | 8/1998 | Mittelmeier et al. |
| 5,792,044 A | 8/1998 | Foley et al. |
| 5,797,909 A | 8/1998 | Michelson |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |

(56) References Cited

U.S. PATENT DOCUMENTS

| | | |
|---|---|---|
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,859,150 A | 1/1999 | Jamiolkowski et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,221 A | 3/1999 | Gelbard |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Tienboon |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,635 A | 9/1999 | Foley et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,976,187 A | 11/1999 | Richelsoph |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Arsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Ehto et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Helmut |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Osken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,049,026 A | 4/2000 | Muschler |
| 6,053,922 A | 4/2000 | Krause et al. |
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,038 A | 8/2000 | Michelson |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |
| 6,139,579 A | 10/2000 | Steffee et al. |

(56) References Cited

U.S. PATENT DOCUMENTS

| | | |
|---|---|---|
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Spinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Tormala et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,342,074 B1 | 1/2002 | Simpson |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |

(56) References Cited

U.S. PATENT DOCUMENTS

| | | |
|---|---|---|
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Mehta et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Kraus |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |

(56) References Cited

U.S. PATENT DOCUMENTS

| | | |
|---|---|---|
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Ll et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,824,565 B2 | 11/2004 | Muhanna et al. |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Ambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |

(56) References Cited

U.S. PATENT DOCUMENTS

| | | |
|---|---|---|
| 7,060,073 B2 | 6/2006 | Frey et al. |
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,053 B2 | 8/2006 | Vanney |
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Ambrecht et al. |
| 7,125,424 B2 | 10/2006 | Banick et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,175,625 B2 | 2/2007 | Culbert |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,482 B2 | 6/2007 | Messerli et al. |
| 7,226,483 B2 | 6/2007 | Gerber et al. |
| 7,235,101 B2 | 6/2007 | Berry et al. |
| 7,238,204 B2 | 7/2007 | Le et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,406,775 B2 | 8/2008 | Funk et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,491,237 B2 | 2/2009 | Randall et al. |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,601,173 B2 | 10/2009 | Messerli et al. |
| 7,608,083 B2 | 10/2009 | Ee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,226 B2 | 2/2010 | Schaller |
| 7,666,266 B2 | 2/2010 | Izawa et al. |
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,686,807 B2 | 3/2010 | Padget et al. |
| 7,691,120 B2 | 4/2010 | Shluzas et al. |
| 7,691,147 B2 | 4/2010 | Guetlin et al. |
| 7,699,878 B2 | 4/2010 | Pavlov et al. |

(56) References Cited

U.S. PATENT DOCUMENTS

| | | |
|---|---|---|
| 7,703,727 B2 | 4/2010 | Selness |
| 7,704,280 B2 | 4/2010 | Echmann et al. |
| 7,708,778 B2 | 5/2010 | Gordon et al. |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |
| 7,763,028 B2 | 7/2010 | Lim et al. |
| 7,763,038 B2 | 7/2010 | O'Brien |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | LeHuec et al. |
| 7,828,849 B2 | 11/2010 | Lim |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,927,373 B2 | 4/2011 | Parsons et al. |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,938,857 B2 | 5/2011 | Garcia-Bengochea et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,377 B2 | 8/2011 | Culbert et al. |
| 7,993,403 B2 | 8/2011 | Foley et al. |
| 7,998,176 B2 | 8/2011 | Culbert |
| 8,007,535 B2 | 8/2011 | Hudgins et al. |
| 8,012,207 B2 | 9/2011 | Kim |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,972 B2 | 2/2012 | Zucherman et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | Delurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,187,332 B2 | 5/2012 | McLuen |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,675 B2 | 7/2012 | Rhoda |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,282,641 B2 | 10/2012 | Lopez et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,313,528 B1 | 11/2012 | Wensel |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,343,222 B2 | 1/2013 | Cope |
| 8,353,961 B2 | 1/2013 | McClintock et al. |
| 8,361,154 B2 | 1/2013 | Reo |
| 8,366,777 B2 | 2/2013 | Matthis et al. |
| 8,377,098 B2 | 2/2013 | Landry et al. |

(56) References Cited

U.S. PATENT DOCUMENTS

| | | |
|---|---|---|
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller et al. |
| 8,454,698 B2 | 6/2013 | De et al. |
| 8,465,524 B2 | 6/2013 | Siegal |
| 8,470,043 B2 | 6/2013 | Schaller et al. |
| 8,480,715 B2 | 7/2013 | Gray |
| 8,480,742 B2 | 7/2013 | Pisharodi |
| 8,480,748 B2 | 7/2013 | Poulos |
| 8,486,109 B2 | 7/2013 | Siegal |
| 8,486,148 B2 | 7/2013 | Butler et al. |
| 8,491,591 B2 | 7/2013 | Sebastian |
| 8,491,653 B2 | 7/2013 | Zucherman et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,545,567 B1 | 10/2013 | Krueger |
| 8,551,092 B2 | 10/2013 | Morgan et al. |
| 8,551,094 B2 | 10/2013 | Von et al. |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,088 B1 | 1/2014 | Tohmeh et al. |
| 8,623,091 B2 | 1/2014 | Suedkamp et al. |
| 8,628,576 B2 | 1/2014 | Triplett et al. |
| 8,628,577 B1 | 1/2014 | Jimenez |
| 8,628,578 B2 | 1/2014 | Miller et al. |
| 8,632,595 B2 | 1/2014 | Weiman |
| 8,636,746 B2 | 1/2014 | Jimenez et al. |
| 8,641,764 B2 | 2/2014 | Gately |
| 8,663,329 B2 | 3/2014 | Ernst |
| 8,663,331 B2 | 3/2014 | McClellan et al. |
| 8,668,740 B2 | 3/2014 | Rhoda et al. |
| 8,672,977 B2 | 3/2014 | Siegal et al. |
| 8,679,161 B2 | 3/2014 | Malandain et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,702,757 B2 | 4/2014 | Thommen et al. |
| 8,702,798 B2 | 4/2014 | Matthis et al. |
| 8,709,086 B2 | 4/2014 | Glerum |
| 8,709,088 B2 | 4/2014 | Kleiner et al. |
| 8,715,284 B2 | 5/2014 | Culbert |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,740,954 B2 | 6/2014 | Ghobrial et al. |
| 8,753,398 B2 | 6/2014 | Gordon et al. |
| 8,758,349 B2 | 6/2014 | Germain et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,733 B2 | 9/2014 | O'Neil et al. |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,900,235 B2 | 12/2014 | Siegal |
| 8,900,307 B2 | 12/2014 | Hawkins et al. |
| 8,906,098 B2 | 12/2014 | Siegal |
| 8,920,506 B2 | 12/2014 | McGuckin, Jr. |
| 8,926,704 B2 | 1/2015 | Glerum et al. |
| 8,936,641 B2 | 1/2015 | Cain |
| 8,940,049 B1 | 1/2015 | Jimenez et al. |
| 8,940,050 B2 | 1/2015 | Laurence et al. |
| 8,940,052 B2 | 1/2015 | Lechmann et al. |
| 8,961,609 B2 | 2/2015 | Schaller |
| 8,968,408 B2 | 3/2015 | Schaller et al. |
| 8,979,860 B2 | 3/2015 | Voellmicke et al. |
| 8,979,929 B2 | 3/2015 | Schaller |
| 8,986,387 B1 | 3/2015 | To et al. |
| 8,986,388 B2 | 3/2015 | Siegal et al. |
| 8,986,389 B2 | 3/2015 | Lim et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,034,041 B2 | 5/2015 | Wolters et al. |
| 9,039,767 B2 | 5/2015 | Raymond et al. |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,101,491 B2 | 8/2015 | Rodgers et al. |
| 9,101,492 B2 | 8/2015 | Mangione et al. |
| 9,107,766 B1 | 8/2015 | McLean et al. |
| 9,119,730 B2 | 9/2015 | Glerum et al. |
| 9,155,631 B2 | 10/2015 | Seifert et al. |
| 9,237,956 B1 | 1/2016 | Jensen |
| 9,254,138 B2 | 2/2016 | Siegal et al. |
| 9,259,326 B2 | 2/2016 | Schaller |
| 9,271,846 B2 | 3/2016 | Lim et al. |
| 9,277,928 B2 | 3/2016 | Morgenstern Lopez |
| 9,282,979 B2 | 3/2016 | O'Neil et al. |
| 9,283,092 B2 | 3/2016 | Siegal et al. |
| 9,295,562 B2 | 3/2016 | Lechmann et al. |
| 9,314,348 B2 | 4/2016 | Emstad |
| 9,320,610 B2 | 4/2016 | Alheidt et al. |
| 9,320,615 B2 | 4/2016 | Suedkamp et al. |
| 9,326,866 B2 | 5/2016 | Schaller et al. |
| 9,333,091 B2 | 5/2016 | DiMauro |
| 9,358,123 B2 | 6/2016 | Remington et al. |
| 9,387,087 B2 | 7/2016 | Tyber |
| 9,387,313 B2 | 7/2016 | Culbert et al. |

(56) References Cited

U.S. PATENT DOCUMENTS

| | | |
|---|---|---|
| 9,402,732 B2 | 8/2016 | Gabelberger |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,934 B2 | 8/2016 | Cain |
| 9,414,936 B2 | 8/2016 | Miller et al. |
| 9,433,510 B2 | 9/2016 | Lechmann et al. |
| 9,439,776 B2 | 9/2016 | DiMauro et al. |
| 9,439,777 B2 | 9/2016 | DiMauro |
| 9,445,825 B2 | 9/2016 | Belaney et al. |
| 9,445,918 B1 | 9/2016 | Lin et al. |
| 9,445,919 B2 | 9/2016 | Palmatier et al. |
| 9,463,099 B2 | 10/2016 | Levy et al. |
| 9,474,623 B2 | 10/2016 | Cain |
| 9,492,288 B2 | 11/2016 | Wagner et al. |
| 9,510,954 B2 | 12/2016 | Glerum et al. |
| 9,522,070 B2 | 12/2016 | Flower et al. |
| 9,526,625 B2 | 12/2016 | Cain |
| 9,532,884 B2 | 1/2017 | Siegal et al. |
| 9,566,165 B2 | 2/2017 | Lee et al. |
| 9,566,167 B2 | 2/2017 | Barrus et al. |
| 9,579,215 B2 | 2/2017 | Suedkamp et al. |
| 9,592,063 B2 | 3/2017 | O'Neil et al. |
| 9,592,129 B2 | 3/2017 | Slivka et al. |
| 9,597,195 B2 | 3/2017 | Cain |
| 9,597,197 B2 | 3/2017 | Lechmann et al. |
| 9,662,223 B2 | 5/2017 | Matthis et al. |
| 9,662,224 B2 | 5/2017 | Weiman et al. |
| 9,675,470 B2 | 6/2017 | Packer et al. |
| 9,717,601 B2 | 8/2017 | Miller |
| 9,724,207 B2 | 8/2017 | DiMauro et al. |
| 9,730,803 B2 | 8/2017 | DiMauro et al. |
| 9,730,806 B2 | 8/2017 | Capote |
| 9,750,552 B2 | 9/2017 | Stephan et al. |
| 9,750,618 B1 | 9/2017 | Daffinson et al. |
| 9,788,962 B2 | 10/2017 | Gabelberger |
| 9,788,963 B2 | 10/2017 | Aquino et al. |
| 9,788,971 B1 | 10/2017 | Stein |
| 9,801,639 B2 | 10/2017 | O'Neil et al. |
| 9,801,640 B2 | 10/2017 | O'Neil et al. |
| 9,801,729 B2 | 10/2017 | DiMauro et al. |
| 9,801,734 B1 | 10/2017 | Stein et al. |
| 9,808,351 B2 | 11/2017 | Kelly et al. |
| 9,808,353 B2 | 11/2017 | Suddaby et al. |
| 9,814,589 B2 | 11/2017 | DiMauro |
| 9,814,590 B2 | 11/2017 | Serhan et al. |
| 9,833,334 B2 | 12/2017 | Voellmicke et al. |
| 9,839,528 B2 | 12/2017 | Weiman et al. |
| 9,839,530 B2 | 12/2017 | Hawkins et al. |
| 9,848,991 B2 | 12/2017 | Boehm et al. |
| 9,872,779 B2 | 1/2018 | Miller et al. |
| 9,895,236 B2 | 2/2018 | Voellmicke et al. |
| 9,907,560 B2 | 3/2018 | O'Neil et al. |
| 9,907,670 B2 | 3/2018 | Deridder et al. |
| 9,913,727 B2 | 3/2018 | Thommen et al. |
| 9,924,978 B2 | 3/2018 | Thommen et al. |
| 9,925,060 B2 | 3/2018 | DiMauro et al. |
| 9,931,223 B2 | 4/2018 | Cain |
| 9,931,226 B2 | 4/2018 | Kurtaliaj et al. |
| 9,937,053 B2 | 4/2018 | Melkent et al. |
| 9,949,769 B2 | 4/2018 | Serhan et al. |
| 9,962,272 B1 | 5/2018 | Daffinson et al. |
| 9,974,664 B2 | 5/2018 | Emerick et al. |
| 9,980,823 B2 | 5/2018 | Matthis et al. |
| 9,980,825 B2 | 5/2018 | Nichols et al. |
| 9,987,143 B2 | 6/2018 | Robinson et al. |
| 9,993,350 B2 | 6/2018 | Cain |
| 10,004,607 B2 | 6/2018 | Weiman et al. |
| 10,034,772 B2 | 7/2018 | Glerum et al. |
| 10,058,433 B2 | 8/2018 | Lechmann et al. |
| 10,085,843 B2 | 10/2018 | Dimauro |
| 10,092,417 B2 | 10/2018 | Weiman et al. |
| 10,098,759 B2 | 10/2018 | Weiman |
| 10,137,009 B2 | 11/2018 | Weiman et al. |
| 10,143,569 B2 | 12/2018 | Weiman et al. |
| 10,166,117 B1 | 1/2019 | Daffinson et al. |
| 10,182,831 B2 | 1/2019 | Marnay et al. |
| 10,219,915 B1 | 3/2019 | Stein |
| 10,238,500 B2 | 3/2019 | Rogers et al. |
| 10,265,191 B2 | 4/2019 | Lim et al. |
| 10,299,934 B2 | 5/2019 | Seifert et al. |
| 10,307,254 B2 | 6/2019 | Levy et al. |
| 10,363,142 B2 | 7/2019 | McClintock et al. |
| 10,376,372 B2 | 8/2019 | Serhan et al. |
| 10,390,963 B2 | 8/2019 | Olmos et al. |
| 10,398,563 B2 | 9/2019 | Engstrom |
| 10,398,566 B2 | 9/2019 | Olmos et al. |
| 10,405,986 B2 | 9/2019 | Kelly et al. |
| 10,405,989 B2 | 9/2019 | O'Neil et al. |
| 10,420,651 B2 | 9/2019 | Serhan et al. |
| 10,426,632 B2 | 10/2019 | Butler et al. |
| 10,433,971 B2 | 10/2019 | DiMauro et al. |
| 10,433,974 B2 | 10/2019 | Michael |
| 10,433,977 B2 | 10/2019 | Lechmann et al. |
| 10,449,056 B2 | 10/2019 | Cain |
| 10,449,057 B2 | 10/2019 | O'Neil et al. |
| 10,449,058 B2 | 10/2019 | Lechmann et al. |
| 10,470,894 B2 | 11/2019 | Foley et al. |
| 10,492,918 B2 | 12/2019 | DiMauro |
| 10,492,924 B2 | 12/2019 | Stein et al. |
| 10,500,062 B2 | 12/2019 | Marchek et al. |
| 10,512,489 B2 | 12/2019 | Serhan et al. |
| 10,537,436 B2 | 1/2020 | Maguire et al. |
| 10,548,741 B2 | 2/2020 | Suedkamp et al. |
| 10,555,817 B2 | 2/2020 | DiMauro et al. |
| 10,575,959 B2 | 3/2020 | DiMauro et al. |
| 10,583,013 B2 | 3/2020 | DiMauro et al. |
| 10,583,015 B2 | 3/2020 | Olmos et al. |
| 10,588,754 B2 | 3/2020 | O'Neil et al. |
| 10,624,758 B2 | 4/2020 | Slivka et al. |
| 10,639,164 B2 | 5/2020 | DiMauro et al. |
| 10,639,166 B2 | 5/2020 | Weiman et al. |
| 10,682,241 B2 | 6/2020 | Glerum et al. |
| 10,743,914 B2 | 8/2020 | Lopez et al. |
| 10,758,371 B2 | 9/2020 | Hessler et al. |
| 10,799,366 B2 | 10/2020 | Davis et al. |
| 10,842,644 B2 | 11/2020 | Weiman et al. |
| 10,888,433 B2 | 1/2021 | Frasier et al. |
| 10,966,840 B2 | 4/2021 | Voellmicke et al. |
| 10,973,652 B2 | 4/2021 | Hawkins et al. |
| 11,051,954 B2 | 7/2021 | Greenhalgh et al. |
| 11,103,362 B2 | 8/2021 | Butler et al. |
| 11,285,018 B2 | 3/2022 | Shoshtaev |
| 11,426,290 B2 | 8/2022 | Miller |
| 11,432,942 B2 | 9/2022 | Olmos et al. |
| 2001/0011174 A1 | 8/2001 | Reiley et al. |
| 2001/0016741 A1 | 8/2001 | Burkus et al. |
| 2001/0016775 A1 | 8/2001 | Scarborough et al. |
| 2001/0037126 A1 | 11/2001 | Stack et al. |
| 2001/0039453 A1 | 11/2001 | Gresser et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045942 A1 | 4/2002 | Ham |
| 2002/0055740 A1 | 5/2002 | Lieberman |
| 2002/0055781 A1 | 5/2002 | Sazy |
| 2002/0068974 A1 | 6/2002 | Kuslich et al. |
| 2002/0072801 A1 | 6/2002 | Michelson |
| 2002/0077701 A1 | 6/2002 | Kuslich |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0138078 A1 | 9/2002 | Chappuis |
| 2002/0143331 A1 | 10/2002 | Zucherman et al. |

(56) References Cited

U.S. PATENT DOCUMENTS

| | | |
|---|---|---|
| 2002/0151976 A1 | 10/2002 | Foley et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173841 A1 | 11/2002 | Ortiz et al. |
| 2002/0173851 A1 | 11/2002 | McKay |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0006942 A1 | 1/2003 | Searls et al. |
| 2003/0014113 A1 | 1/2003 | Ralph et al. |
| 2003/0014116 A1 | 1/2003 | Ralph et al. |
| 2003/0023305 A1 | 1/2003 | McKay |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0050644 A1 | 3/2003 | Boucher et al. |
| 2003/0063582 A1 | 4/2003 | Mizell et al. |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074075 A1 | 4/2003 | Thomas et al. |
| 2003/0078667 A1 | 4/2003 | Manasas et al. |
| 2003/0108588 A1 | 6/2003 | Chen et al. |
| 2003/0130664 A1 | 7/2003 | Boucher et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0171812 A1 | 9/2003 | Grunberg et al. |
| 2003/0187431 A1 | 10/2003 | Simonson |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0208122 A1 | 11/2003 | Melkent et al. |
| 2003/0208203 A1 | 11/2003 | Lim et al. |
| 2003/0208220 A1 | 11/2003 | Worley et al. |
| 2003/0208270 A9 | 11/2003 | Michelson |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034429 A1 | 2/2004 | Lambrecht et al. |
| 2004/0049190 A1 | 3/2004 | Biedermann et al. |
| 2004/0049223 A1 | 3/2004 | Nishtala et al. |
| 2004/0049270 A1 | 3/2004 | Gewirtz |
| 2004/0059333 A1 | 3/2004 | Carl et al. |
| 2004/0059337 A1 | 3/2004 | Hanson et al. |
| 2004/0059350 A1 | 3/2004 | Gordon et al. |
| 2004/0059418 A1 | 3/2004 | McKay et al. |
| 2004/0068269 A1 | 4/2004 | Bonati et al. |
| 2004/0073213 A1 | 4/2004 | Serhan et al. |
| 2004/0082953 A1 | 4/2004 | Petit |
| 2004/0083000 A1 | 4/2004 | Keller et al. |
| 2004/0087947 A1 | 5/2004 | Lim et al. |
| 2004/0088055 A1 | 5/2004 | Hanson et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Oshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106940 A1 | 6/2004 | Shaolian et al. |
| 2004/0116997 A1 | 6/2004 | Taylor et al. |
| 2004/0117022 A1 | 6/2004 | Marnay et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193271 A1 | 9/2004 | Fraser et al. |
| 2004/0193277 A1 | 9/2004 | Long et al. |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0243229 A1 | 12/2004 | Vidlund et al. |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |

(56) References Cited

U.S. PATENT DOCUMENTS

| | | |
|---|---|---|
| 2004/0267367 A1 | 12/2004 | O'Neil |
| 2005/0004578 A1 | 1/2005 | Lambrecht et al. |
| 2005/0010292 A1 | 1/2005 | Carrasco |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0027360 A1 | 2/2005 | Webb et al. |
| 2005/0033295 A1 | 2/2005 | Wisnewski |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Michael John |
| 2005/0090833 A1 | 4/2005 | DiPoto |
| 2005/0090852 A1 | 4/2005 | Ayne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113916 A1 * | 5/2005 | Branch, Jr. ............. A61F 2/447 623/17.11 |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0149022 A1 | 7/2005 | Shaolian et al. |
| 2005/0149030 A1 | 7/2005 | Serhan et al. |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0165398 A1 | 7/2005 | Reiley |
| 2005/0165420 A1 | 7/2005 | Cha |
| 2005/0165484 A1 | 7/2005 | Ferree |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde |
| 2005/0278029 A1 | 12/2005 | Trieu |
| 2005/0283238 A1 | 12/2005 | Reiley |
| 2005/0287071 A1 | 12/2005 | Wenz |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |

(56) References Cited

U.S. PATENT DOCUMENTS

| | | |
|---|---|---|
| 2006/0058790 A1 | 3/2006 | Carl et al. |
| 2006/0058807 A1 | 3/2006 | Landry et al. |
| 2006/0058880 A1 | 3/2006 | Wysocki et al. |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |
| 2006/0119629 A1 | 6/2006 | An et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | Dinello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149229 A1 | 7/2006 | Kwak et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Ambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247771 A1 | 11/2006 | Peterman et al. |
| 2006/0247781 A1 | 11/2006 | Francis |
| 2006/0253120 A1 | 11/2006 | Anderson et al. |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Ambrecht et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |

(56) References Cited

U.S. PATENT DOCUMENTS

| | | |
|---|---|---|
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Eung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118222 A1 | 5/2007 | Philipp |
| 2007/0118223 A1 | 5/2007 | Allard et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |
| 2007/0162132 A1 | 7/2007 | Messerli |
| 2007/0162138 A1 | 7/2007 | Heinz |
| 2007/0167945 A1 | 7/2007 | Ange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Trieu |
| 2007/0233083 A1 | 10/2007 | Abdou |
| 2007/0233089 A1 | 10/2007 | Dipoto et al. |
| 2007/0233130 A1 | 10/2007 | Suddaby |
| 2007/0233244 A1 | 10/2007 | Lopez et al. |
| 2007/0233254 A1 | 10/2007 | Grotz et al. |
| 2007/0250167 A1 | 10/2007 | Bray et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Trieu et al. |
| 2007/0270954 A1 | 11/2007 | Wu |
| 2007/0270957 A1 | 11/2007 | Heinz |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | De et al. |
| 2007/0288091 A1 | 12/2007 | Braddock et al. |
| 2008/0009877 A1 | 1/2008 | Sankaran et al. |
| 2008/0015694 A1 | 1/2008 | Tribus |
| 2008/0021556 A1 | 1/2008 | Edie |
| 2008/0021557 A1 | 1/2008 | Trieu |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |
| 2008/0027454 A1 | 1/2008 | Johnson et al. |
| 2008/0027544 A1 | 1/2008 | Melkent |
| 2008/0027550 A1 | 1/2008 | Ink et al. |
| 2008/0045966 A1 | 2/2008 | Buttermann et al. |
| 2008/0051890 A1 | 2/2008 | Waugh et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0097454 A1 | 4/2008 | Deridder et al. |
| 2008/0097611 A1 | 4/2008 | Mastrorio et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0132934 A1 | 6/2008 | Reiley et al. |
| 2008/0133012 A1 | 6/2008 | McGuckin |
| 2008/0133017 A1 | 6/2008 | Beyar et al. |
| 2008/0140085 A1 | 6/2008 | Gately et al. |
| 2008/0147129 A1 | 6/2008 | Biedermann et al. |
| 2008/0154377 A1 | 6/2008 | Voellmicke |
| 2008/0154379 A1 | 6/2008 | Steiner et al. |
| 2008/0161927 A1 | 7/2008 | Savage et al. |
| 2008/0167657 A1 | 7/2008 | Greenhalgh |
| 2008/0172128 A1 | 7/2008 | Perez-Cruet et al. |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195210 A1 | 8/2008 | Milijasevic et al. |
| 2008/0208344 A1 | 8/2008 | Kilpela et al. |
| 2008/0221586 A1 | 9/2008 | Garcia-Bengochea et al. |
| 2008/0221687 A1 | 9/2008 | Viker |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0312743 A1 | 12/2008 | Vila et al. |
| 2008/0319477 A1 | 12/2008 | Justis et al. |
| 2009/0005873 A1 | 1/2009 | Slivka et al. |
| 2009/0018524 A1 | 1/2009 | Greenhalgh et al. |

(56) References Cited

U.S. PATENT DOCUMENTS

| | | |
|---|---|---|
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | Von et al. |
| 2009/0069895 A1 | 3/2009 | Gittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Owry et al. |
| 2009/0105712 A1 | 4/2009 | Dauster et al. |
| 2009/0105745 A1 | 4/2009 | Culbert |
| 2009/0112217 A1 | 4/2009 | Hester |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0198339 A1 | 8/2009 | Kleiner et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0234364 A1 | 9/2009 | Crook |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van et al. |
| 2010/0042218 A1 | 2/2010 | Nebosky et al. |
| 2010/0049324 A1 | 2/2010 | Valdevit et al. |
| 2010/0057204 A1 | 3/2010 | Kadaba et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga et al. |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0106251 A1 | 4/2010 | Kast |
| 2010/0114105 A1 | 5/2010 | Butters et al. |
| 2010/0114147 A1 | 5/2010 | Biyani |
| 2010/0125334 A1 | 5/2010 | Krueger |
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0241231 A1 | 9/2010 | Marino et al. |
| 2010/0249935 A1 | 9/2010 | Slivka et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0274358 A1 | 10/2010 | Mueller et al. |
| 2010/0280619 A1 | 11/2010 | Yuan et al. |
| 2010/0286777 A1 | 11/2010 | Errico et al. |
| 2010/0292700 A1 | 11/2010 | Ries |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0324683 A1 | 12/2010 | Reichen et al. |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | McManus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0040332 A1 | 2/2011 | Culbert et al. |
| 2011/0046674 A1 | 2/2011 | Calvosa et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160866 A1 | 6/2011 | Aurence et al. |
| 2011/0172716 A1 | 7/2011 | Glerum |
| 2011/0190816 A1 | 8/2011 | Sheffer et al. |
| 2011/0190891 A1 | 8/2011 | Suh et al. |
| 2011/0230971 A1 | 9/2011 | Donner et al. |
| 2011/0238072 A1 | 9/2011 | Tyndall |
| 2011/0251690 A1 | 10/2011 | Berger et al. |
| 2011/0270261 A1 | 11/2011 | Mast et al. |
| 2011/0276142 A1 | 11/2011 | Niemiec et al. |
| 2011/0282459 A1 | 11/2011 | McClellan et al. |
| 2011/0301712 A1* | 12/2011 | Palmatier ............ A61F 2/4611 623/17.16 |
| 2011/0307010 A1 | 12/2011 | Pradhan |
| 2011/0313465 A1 | 12/2011 | Warren et al. |
| 2011/0320000 A1 | 12/2011 | O'Neil et al. |
| 2012/0004726 A1 | 1/2012 | Greenhalgh et al. |
| 2012/0004732 A1 | 1/2012 | Goel et al. |
| 2012/0006361 A1 | 1/2012 | Miyagi et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029639 A1 | 2/2012 | Blackwell et al. |
| 2012/0035730 A1 | 2/2012 | Spann |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0109319 A1 | 5/2012 | Perisic |
| 2012/0123546 A1 | 5/2012 | Medina |
| 2012/0136443 A1 | 5/2012 | Wenzel |
| 2012/0150304 A1 | 6/2012 | Glerum et al. |

(56) References Cited

U.S. PATENT DOCUMENTS

| | | |
|---|---|---|
| 2012/0150305 A1 | 6/2012 | Glerum et al. |
| 2012/0158146 A1 | 6/2012 | Glerum et al. |
| 2012/0158148 A1 | 6/2012 | Glerum et al. |
| 2012/0191204 A1 | 7/2012 | Bae et al. |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0253395 A1 | 10/2012 | Linares |
| 2012/0253406 A1 | 10/2012 | Bae et al. |
| 2012/0277869 A1 | 11/2012 | Siccardi et al. |
| 2012/0277877 A1 | 11/2012 | Smith et al. |
| 2012/0283837 A1 | 11/2012 | Bae et al. |
| 2012/0310350 A1 | 12/2012 | Farris et al. |
| 2012/0310352 A1 | 12/2012 | DiMauro et al. |
| 2012/0323327 A1 | 12/2012 | McAfee |
| 2012/0330421 A1 | 12/2012 | Weiman |
| 2013/0006362 A1 | 1/2013 | Biedermann et al. |
| 2013/0023937 A1 | 1/2013 | Biedermann et al. |
| 2013/0053966 A1 | 2/2013 | Jimenez et al. |
| 2013/0060337 A1 | 3/2013 | Petersheim et al. |
| 2013/0073044 A1 | 3/2013 | Gamache |
| 2013/0079790 A1 | 3/2013 | Stein et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0150906 A1 | 6/2013 | Kerboul et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0218276 A1 | 8/2013 | Fiechter et al. |
| 2013/0231747 A1 | 9/2013 | Olmos et al. |
| 2013/0238006 A1 | 9/2013 | O'Neil et al. |
| 2013/0253585 A1 | 9/2013 | Garcia et al. |
| 2013/0261746 A1 | 10/2013 | Linares et al. |
| 2013/0261747 A1 | 10/2013 | Geisert |
| 2013/0268077 A1 | 10/2013 | You et al. |
| 2013/0274883 A1 | 10/2013 | McLuen et al. |
| 2013/0310937 A1 | 11/2013 | Luiz |
| 2013/0310939 A1 | 11/2013 | Fabian et al. |
| 2013/0325128 A1 | 12/2013 | Perloff et al. |
| 2014/0018816 A1 | 1/2014 | Fenn et al. |
| 2014/0039622 A1 | 2/2014 | Glerum et al. |
| 2014/0039626 A1 | 2/2014 | Mitchell |
| 2014/0046333 A1 | 2/2014 | Johnson et al. |
| 2014/0046446 A1 | 2/2014 | Robinson |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0067073 A1 | 3/2014 | Hauck |
| 2014/0081267 A1 | 3/2014 | Orsak et al. |
| 2014/0086962 A1 | 3/2014 | Jin et al. |
| 2014/0094916 A1* | 4/2014 | Glerum .............. A61F 2/442 623/17.15 |
| 2014/0094917 A1 | 4/2014 | Salerni |
| 2014/0100662 A1 | 4/2014 | Patterson et al. |
| 2014/0107790 A1 | 4/2014 | Combrowski |
| 2014/0114414 A1 | 4/2014 | Abdou et al. |
| 2014/0121774 A1 | 5/2014 | Glerum et al. |
| 2014/0128977 A1 | 5/2014 | Glerum et al. |
| 2014/0128980 A1 | 5/2014 | Kirschman |
| 2014/0135930 A1 | 5/2014 | Georges |
| 2014/0135934 A1 | 5/2014 | Hansell et al. |
| 2014/0142706 A1 | 5/2014 | Hansell et al. |
| 2014/0148904 A1 | 5/2014 | Robinson |
| 2014/0163682 A1 | 6/2014 | Lott et al. |
| 2014/0172103 A1 | 6/2014 | O'Neil et al. |
| 2014/0172105 A1 | 6/2014 | Frasier et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0243892 A1 | 8/2014 | Choinski |
| 2014/0243981 A1 | 8/2014 | Davenport et al. |
| 2014/0249629 A1 | 9/2014 | Moskowitz et al. |
| 2014/0249630 A1 | 9/2014 | Weiman |
| 2014/0249632 A1 | 9/2014 | Weiman |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277473 A1 | 9/2014 | Perrow |
| 2014/0277476 A1 | 9/2014 | McLean et al. |
| 2014/0277481 A1 | 9/2014 | Lee et al. |
| 2014/0277507 A1 | 9/2014 | Baynham |
| 2014/0296983 A1 | 10/2014 | Fauth et al. |
| 2014/0303731 A1 | 10/2014 | Glerum |
| 2014/0303732 A1 | 10/2014 | Rhoda et al. |
| 2014/0336764 A1 | 11/2014 | Masson et al. |
| 2014/0343678 A1 | 11/2014 | Suddaby et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0051701 A1* | 2/2015 | Glerum .............. A61F 2/447 623/17.16 |
| 2015/0057755 A1 | 2/2015 | Suddaby et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094813 A1 | 4/2015 | Lechmann et al. |
| 2015/0094814 A1 | 4/2015 | Emerick et al. |
| 2015/0100128 A1 | 4/2015 | Glerum et al. |
| 2015/0112398 A1 | 4/2015 | Morgenstern et al. |
| 2015/0112438 A1 | 4/2015 | McLean |
| 2015/0182347 A1 | 7/2015 | Robinson |
| 2015/0190242 A1 | 7/2015 | Blain et al. |
| 2015/0196400 A1 | 7/2015 | Dace |
| 2015/0216671 A1 | 8/2015 | Cain |
| 2015/0230929 A1 | 8/2015 | Lorio |
| 2015/0230932 A1 | 8/2015 | Schaller |
| 2015/0238324 A1 | 8/2015 | Nebosky et al. |
| 2015/0250606 A1 | 9/2015 | McLean |
| 2015/0257894 A1 | 9/2015 | Levy et al. |
| 2015/0272743 A1 | 10/2015 | Jimenez et al. |
| 2015/0305881 A1 | 10/2015 | Bal et al. |
| 2015/0320571 A1 | 11/2015 | Lechmann et al. |
| 2016/0016309 A1 | 1/2016 | Swift et al. |
| 2016/0022438 A1 | 1/2016 | Lamborne et al. |
| 2016/0038301 A1 | 2/2016 | Wickham |
| 2016/0045333 A1 | 2/2016 | Baynham |
| 2016/0051373 A1 | 2/2016 | Faulhaber |
| 2016/0051374 A1 | 2/2016 | Faulhaber |
| 2016/0067055 A1 | 3/2016 | Hawkins et al. |
| 2016/0081814 A1 | 3/2016 | Baynham |
| 2016/0100951 A1 | 4/2016 | Suddaby et al. |
| 2016/0100954 A1 | 4/2016 | Rumi et al. |
| 2016/0106551 A1 | 4/2016 | Grimberg et al. |
| 2016/0120662 A1 | 5/2016 | Schaller |
| 2016/0128843 A1 | 5/2016 | Tsau et al. |
| 2016/0199195 A1 | 7/2016 | Hauck et al. |
| 2016/0199196 A1 | 7/2016 | Serhan et al. |
| 2016/0228258 A1 | 8/2016 | Schaller et al. |
| 2016/0235455 A1 | 8/2016 | Wahl |
| 2016/0256291 A1 | 9/2016 | Miller |
| 2016/0317714 A1 | 11/2016 | DiMauro et al. |
| 2016/0367265 A1 | 12/2016 | Morgenstern Lopez |
| 2017/0056179 A1 | 3/2017 | Lorio |
| 2017/0095341 A1 | 4/2017 | Smith |

(56) References Cited

U.S. PATENT DOCUMENTS

| | | |
|---|---|---|
| 2017/0100177 A1 | 4/2017 | Kim |
| 2017/0100255 A1 | 4/2017 | Hleihil et al. |
| 2017/0100260 A1 | 4/2017 | Duffield et al. |
| 2017/0119542 A1 | 5/2017 | Logan et al. |
| 2017/0128226 A1 | 5/2017 | Faulhaber |
| 2017/0209284 A1 | 7/2017 | Overes et al. |
| 2017/0216045 A1 | 8/2017 | Dewey et al. |
| 2017/0216046 A1 | 8/2017 | Greenhalgh et al. |
| 2017/0266015 A1 | 9/2017 | Overes et al. |
| 2017/0290675 A1 | 10/2017 | Olmos et al. |
| 2017/0290677 A1 | 10/2017 | Olmos et al. |
| 2017/0296352 A1 | 10/2017 | Richerme et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0071111 A1 | 3/2018 | Sharifi-Mehr et al. |
| 2018/0116811 A1 | 5/2018 | Bernard et al. |
| 2018/0161175 A1 | 6/2018 | Frasier et al. |
| 2018/0193164 A1 | 7/2018 | Shoshtaev |
| 2018/0256360 A1 | 9/2018 | Cain |
| 2018/0256362 A1 | 9/2018 | Slivka et al. |
| 2018/0360616 A1 | 12/2018 | Luu |
| 2019/0008654 A1 | 1/2019 | Thommen |
| 2019/0021868 A1 | 1/2019 | Ludwig et al. |
| 2019/0083276 A1 | 3/2019 | DiMauro |
| 2019/0105171 A1 | 4/2019 | Rogers et al. |
| 2019/0117409 A1 | 4/2019 | Shoshtaev |
| 2019/0133785 A1 | 5/2019 | Georges |
| 2019/0142602 A1 | 5/2019 | Olmos et al. |
| 2019/0254836 A1 | 8/2019 | Cowan et al. |
| 2019/0269521 A1 | 9/2019 | Shoshtaev |
| 2019/0336301 A1 | 11/2019 | Engstrom |
| 2019/0388238 A1 | 12/2019 | Lechmann et al. |
| 2020/0008950 A1 | 1/2020 | Serhan et al. |
| 2020/0015982 A1 | 1/2020 | O'Neil |
| 2020/0030114 A1 | 1/2020 | Cain |
| 2020/0060843 A1 | 2/2020 | Evans et al. |
| 2020/0078190 A1 | 3/2020 | Rogers et al. |
| 2020/0078192 A1 | 3/2020 | Marchek et al. |
| 2020/0129307 A1 | 4/2020 | Hunziker et al. |
| 2020/0129308 A1 | 4/2020 | Suedkamp et al. |
| 2020/0297506 A1 | 9/2020 | Olmos et al. |
| 2020/0375754 A1 | 12/2020 | Cain |
| 2020/0375755 A1 | 12/2020 | Cain |
| 2020/0383799 A1 | 12/2020 | Cain |
| 2020/0405497 A1 | 12/2020 | Olmos et al. |
| 2020/0405500 A1 | 12/2020 | Cain |
| 2021/0000160 A1 | 1/2021 | Olmos et al. |
| 2021/0077272 A1 | 3/2021 | Eisen et al. |
| 2021/0101585 A1 | 4/2021 | Son et al. |
| 2021/0177619 A1 | 6/2021 | Voellmicke et al. |
| 2021/0186706 A1 | 6/2021 | Spitler et al. |
| 2021/0353427 A1 | 11/2021 | Butler et al. |
| 2022/0313450 A1 | 10/2022 | Donohoe et al. |
| 2022/0401225 A1 | 12/2022 | Miller |
| 2022/0409395 A1 | 12/2022 | Hunziker et al. |
| 2023/0019591 A1 | 1/2023 | Rogers et al. |
| 2023/0026598 A1 | 1/2023 | Weiman et al. |

FOREIGN PATENT DOCUMENTS

| | | |
|---|---|---|
| CA | 2617872 A1 | 2/2007 |
| CN | 1177918 A | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 102164552 A | 8/2011 |
| CN | 103620249 A | 3/2014 |
| CN | 104023674 A | 9/2014 |
| CN | 104023675 A | 9/2014 |
| CN | 104042366 A | 9/2014 |
| CN | 104822332 A | 8/2015 |
| CN | 104921848 A | 9/2015 |
| CN | 104939876 A | 9/2015 |
| CN | 105025846 A | 11/2015 |
| CN | 105188582 A | 12/2015 |
| CN | 204971722 U | 1/2016 |
| CN | 105769391 A | 7/2016 |
| CN | 105769392 A | 7/2016 |
| CN | 107205829 A | 9/2017 |
| CN | 107510524 A | 12/2017 |
| DE | 2804936 A1 | 8/1979 |
| DE | 3023353 A1 | 4/1981 |
| DE | 3801459 A1 | 8/1989 |
| DE | 3911610 A1 | 10/1990 |
| DE | 4012622 C1 | 7/1991 |
| DE | 9407806 U1 | 7/1994 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| DE | 10357960 B4 | 9/2015 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0509084 A1 | 10/1992 |
| EP | 0525352 A1 | 2/1993 |
| EP | 0529275 A2 | 3/1993 |
| EP | 0609084 A2 | 8/1994 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1103236 A2 | 5/2001 |
| EP | 1121906 A2 | 8/2001 |
| EP | 1157676 A1 | 11/2001 |
| EP | 1283026 A2 | 2/2003 |
| EP | 1290985 A2 | 3/2003 |
| EP | 1308132 A2 | 5/2003 |
| EP | 1374784 A1 | 1/2004 |
| EP | 1378205 A1 | 1/2004 |
| EP | 1405602 A1 | 4/2004 |
| EP | 1532949 A1 | 5/2005 |
| EP | 1541096 A1 | 6/2005 |
| EP | 1605836 A1 | 12/2005 |
| EP | 1385449 B1 | 7/2006 |
| EP | 1683490 A2 | 7/2006 |
| EP | 1683593 A2 | 7/2006 |
| EP | 1698305 A1 | 9/2006 |
| EP | 1829486 A1 | 9/2007 |
| EP | 1843723 A1 | 10/2007 |
| EP | 1845874 A1 | 10/2007 |
| EP | 1924227 A2 | 5/2008 |
| EP | 1925272 | 5/2008 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2699065 A1 | 2/2014 |
| EP | 2705809 A1 | 3/2014 |
| EP | 2764851 A1 | 8/2014 |
| EP | 2777633 | 9/2014 |
| EP | 2645965 B1 | 8/2016 |
| EP | 3263072 A1 | 1/2018 |
| EP | 3366263 A1 | 8/2018 |
| ES | 2361099 A1 | 6/2011 |
| FR | 2634260 A1 | 1/1990 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |

(56) References Cited

FOREIGN PATENT DOCUMENTS

| | | |
|---|---|---|
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| FR | 2948277 | 1/2011 |
| FR | 3026294 | 4/2016 |
| GB | 0457673 A | 12/1936 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 07-213533 A | 8/1995 |
| JP | 10-085232 A | 4/1998 |
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-501901 A | 1/2006 |
| JP | 2006-516456 | 7/2006 |
| JP | 2007-054666 A | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508048 A | 4/2012 |
| JP | 4988203 B2 | 8/2012 |
| JP | 2013-508031 | 3/2013 |
| JP | 5164571 B2 | 3/2013 |
| JP | 2014-502867 A | 2/2014 |
| JP | 2015-500707 A | 1/2015 |
| JP | 2015-525652 A | 9/2015 |
| JP | 2017-505196 A | 2/2017 |
| KR | 20-0290058 Y1 | 9/2002 |
| WO | 91/09572 A1 | 7/1991 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | 99/42062 A1 | 8/1999 |
| WO | 99/52478 A1 | 10/1999 |
| WO | 99/53871 A1 | 10/1999 |
| WO | 99/60956 A1 | 12/1999 |
| WO | 99/62417 A1 | 12/1999 |
| WO | 99/63914 A1 | 12/1999 |
| WO | 00/12033 | 3/2000 |
| WO | 00/13620 A1 | 3/2000 |
| WO | 00/24343 A1 | 5/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/80751 A1 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/45627 A1 | 6/2002 |
| WO | 02/47563 A1 | 6/2002 |
| WO | 02/71921 A2 | 9/2002 |
| WO | 2002/085250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/03951 A1 | 6/2003 |
| WO | 2003/101308 A1 | 12/2003 |
| WO | 2004/008949 A2 | 1/2004 |
| WO | 03/59180 A2 | 3/2004 |
| WO | 2004/034924 A2 | 4/2004 |
| WO | 2004/062505 A1 | 7/2004 |
| WO | 2004/064603 A2 | 8/2004 |
| WO | 2004/069033 A2 | 8/2004 |
| WO | 2004/078220 A2 | 9/2004 |
| WO | 2004/078221 A2 | 9/2004 |
| WO | 2004/079221 A1 | 9/2004 |
| WO | 2004/080316 A1 | 9/2004 |
| WO | 2004/082526 A2 | 9/2004 |
| WO | 04/93749 A1 | 11/2004 |
| WO | 2004/098420 A2 | 11/2004 |
| WO | 2004/098453 A2 | 11/2004 |
| WO | 2004/108022 A1 | 12/2004 |
| WO | 2005/020861 A1 | 3/2005 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/112834 A2 | 12/2005 |
| WO | 2005/112835 A2 | 12/2005 |
| WO | 2005/115261 A1 | 12/2005 |
| WO | 2006/017507 A2 | 2/2006 |
| WO | 2006/044920 A2 | 4/2006 |
| WO | 2006/047587 A2 | 5/2006 |
| WO | 2006/047645 A2 | 5/2006 |
| WO | 2006/058079 A2 | 6/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/078972 A2 | 7/2006 |
| WO | 2006/081843 A1 | 8/2006 |
| WO | 2006/108067 A2 | 10/2006 |
| WO | 2006/118944 A1 | 11/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/004057 A2 | 1/2008 |
| WO | 2008/005627 A1 | 1/2008 |
| WO | 2008/011378 A1 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |

(56) References Cited

FOREIGN PATENT DOCUMENTS

| WO | 2009/092102 A1 | 7/2009 |
|---|---|---|
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/011348 A1 | 1/2010 |
| WO | 2010/068725 A2 | 6/2010 |
| WO | 2010/075451 A1 | 7/2010 |
| WO | 2010/075555 A2 | 7/2010 |
| WO | 2010/088766 A1 | 8/2010 |
| WO | 2010/121002 A1 | 10/2010 |
| WO | 2010/136170 A1 | 12/2010 |
| WO | 2010/148112 A1 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | 2011/079910 A2 | 7/2011 |
| WO | 2011/119617 A1 | 9/2011 |
| WO | 2011/142761 A1 | 11/2011 |
| WO | 2011/150350 A1 | 12/2011 |
| WO | 2012/009152 A1 | 1/2012 |
| WO | 2012/027490 A2 | 3/2012 |
| WO | 2012/028182 A1 | 3/2012 |
| WO | 2012/030331 A1 | 3/2012 |
| WO | 2012/089317 A1 | 7/2012 |
| WO | 2012/103254 A2 | 8/2012 |
| WO | 2012/122294 A1 | 9/2012 |
| WO | 2012/129197 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/148176 A1 | 10/2013 |
| WO | 2013/149611 A1 | 10/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/004660 A1 | 1/2015 |
| WO | 2015/013479 A2 | 1/2015 |
| WO | 2015/022039 A1 | 2/2015 |
| WO | 2015/048997 A1 | 4/2015 |
| WO | 2016/069796 A1 | 5/2016 |
| WO | 2016/118246 A1 | 7/2016 |
| WO | 2016/127139 A1 | 8/2016 |
| WO | 2017/040881 A1 | 3/2017 |
| WO | 2017/066226 A1 | 4/2017 |
| WO | 2017/136620 A1 | 8/2017 |
| WO | 2018/078148 A1 | 5/2018 |

OTHER PUBLICATIONS

Alfen et al., "Developments in the area of Endoscopic Spine Surgery", European Musculoskeletal Review 2006, pp. 23-24, Thessys(Trademark), Transforaminal Endoscopic Spine Systems, joimax Medical Solutions.
Allcock, "Polyphosphazenes", The Encyclopedia of Polymer Science, vol. 13, pp. 31-41, Wiley Intersciences, John Wiley & Sons, (1988).
Apr. 19, 2007 Office Action Communication for Application No. 02719402.6 filed on Mar. 29, 2002.
Brochure for PERPOS PLS System Surgical Technique by Interventional Spine, 2008, 8 pages.
Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997; 21(3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc's Orthopedic WISORD (TM) Malleolar Screw (online), Jul. 30, 2002 (retrieved on Oct. 14, 2003), retrieved from the internet URL. http://www.cambridgescienfiticicinc.com.
Carrino, John A., Roxanne Chan and Alexander R. Vaccaro, "Vertebral Augmentation: Vertebroplasty and Kyphoplasty", Seminars in Roentgenology, vol. 39, No. 1 (January), 2004: pp. 68-84.
Cheng, B.C., Ph.D., Biomechanical pullout strength and histology of Plasmapore Registered XP coated implant:, Ovine multi time point survival study. Aesculap Impact Systems, LLC, 2013, 12 pages.
Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.
Chin, "Early Results of the Triage Medical Percutaneous Transfacet Pedicular BONE-LOK Compression Device for Lumbar Fusion", Accessed online Jul. 10, 2017, 10 pages.
CN Office Action Mailed on Apr. 24, 2020 for ON Application No. 201780040910.
Cohn, "Biodegradable PEO/PLA Block Copolymers"; Journal of Biomedical Materials Research; 1988; pp. 993-1009; vol. 22; John Wiley & Sons, Inc.
Cohn, "Polymer Preprints", ACS Division of Polymer Chemistry, vol. 30(1), 1989, p. 498, (e.g. PEO/PLA).
Edeland, H.G., "Some Additional Suggestions for an Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998; 212:119-132.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Fuchs, "The use of an interspinous implant in conjuction with a graded facetectomy procedure", Spine vol. 30, No. 11, pp. 1266-1272, 2005.
Gore, "Technique of Cervical Interbody Fusion", Clinical Orthopaedics and Related Research, Sep. 1984, pp. 191-195, No. 188.
Gray's Anatomy, Crown Publishers, Inc., 1977, pp. 33-54.
Ha, S. W. et al., Topographical characterization and microstructural interface analysis of vacuum-plasma-sprayed titanium and hydroxyapatite coatings on carbon fibre-reinforced poly(etheretherketone), J. Mater. Sci.: Materials in Medicine, 1997, v. 8, pp. 891-896.
Haas, Norbert P., New Products from AO Development [online], May 2002 [retrieved on Oct. 14, 2003], Retrieved from the Internet <URL: http://www.ao.asif.ch/development/pdf_tk_news_02.pdf>.
Hao et al., Investigation of nanocomposites based on semi-interpenetrating network of [L—poly (epsilon-caprolactone )]/[net-poly (epsilon-caprolactone)] and hydroxyapatite nanocrystals. Biomaterials. Apr. 2003; 24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992; 13(1):69-80.

(56) References Cited

OTHER PUBLICATIONS

Heller in Handbook of Biodegradable Polymers, edited by Domb, et al., Hardwood Academic Press, pp. 99-118 (1997).
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.
Hunt, "Expandable Cage Placement Via a Posterolateral Approach in Lumbar Spine Reconstructions", Journal of Neurosurgery: Spine, Sep. 2006, pp. 271-274, vol. 5.
International Patent Application No. PCT /US2013/029014, International Search Report dated Jul. 1, 2013, 7 pages.
International Search Report received in PCT application No. PCT/US2007/086866 dated Jul. 7, 2008, 2 pages.
Iprenburg et al., "Transforaminal Endoscopic Surgery in Lumbar Disc Herniation in an Economic Crisis—The TESSYS Method", US Musculoskeletal, 2008, p. 47-49.
Japanese Office Action for Application No. 2013-542047, dated Sep. 8, 2015 (12 pages).
Japanese Office Action for Application No. 2016-135826, dated Jun. 6, 2017, (7 pages).
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kambin et al., "Percutaneous Lateral Discectomy of the Lumbar Spine: A Preliminary Report", Clin. Orthop,: 1983, 174: 127-132.
Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).
Kemnitzer et al., "Degradable Polymers Derived From the Amino Acid L-Tyrozine", The Handbook of Biodegradable Polymers, edited by Domb, et al., Hardwood Academic Press, 1997, pp. 251-272.
Khoo, "Minimally Invasive Correction of Grade I and II Isthmic Spondylolisthesis using AxiaLIF for L5/S1 Fusion", pp. 1-7, Rev B Sep. 15, 2008.
King., "Internal Fixation for Lumbosacral Fusion", The Journal of Bone and Joint Surgery, J. Bone Joint Surg. Am., 1948; 30: 560-578.
Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. (German language document/Engl. summary).
Krbec, "Replacement of the vertebral body with an expansion implant (Synex)", Acta Chir Orthop Traumatol Cech., 2002, pp. 158-162, vol. 69(3) (only Abstract available).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001; 98(3):842-7. Epub Jan. 23, 2001.
Link SB Charite Brochure—Intervertebral Prosthesis 1988, 29 pages.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
U.S. Appl. No. 16/842,058, filed Apr. 7, 2020.
US 5,545,827, 10/1995, Aust (withdrawn)
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.

McAfee et al., Minimally invasive anterior retroperitoneal approach to the lumbar spine: Emphasis on the lateral BAK. Spine. 1998; 23(13): 1476-84.
Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Mendez et al., Self-curing acrylic formulations containing PMMA/PCL composites: properties and antibiotic release behavior. J Biomed Mater Res. Jul. 2002;61 (1 ):66-74.
Morgenstern R; "Transforaminal Endoscopic Stenosis Surgery—A Comparative Study of Laser and Reamed Foraminoplasty", in European Musculoskeletal Review, Issue 1, 2009.
Nguyen et al., Poly(Aryl-Ether-Ether-Ketone) and its Advanced Composites: A Review, Polymer Composites, April 1987, vol. 8, No. 2, pp. 57-73.
Niosi, "Biomechanical characterization of the three-dimentional kinematic behaviour of the Dynesys dynamic stabilization system: an in vitro study", Eur Spine J (2006) 15: pp. 913-922.
Osteoset Registered DBM Pellets (Important Medical Information) [online], Nov. 2002 [retrieved on Oct. 14, 2003]. Retrieved from the Internet <URL: http://www.wmt.com/Literature>.
Polikeit, "The Imporiance of the Endplate for Inlerbody Cages in the Lumbar Spine", Eur. Spine J., 2003, pp. 556-561, vol. 12.
ProMap TM EMG Navigation Probe. Technical Brochure Spineology Inc, Dated May 2009.
Regan et al., Endoscopic thoracic fusion cage. Atlas of Endoscopic Spine Surgery. Quality Medical Publishing, Inc. 1995; 350-354.
Shin, "Posterior Lumbar lnterbody Fusion via a Unilateral Approach", Yonsei Medical Journal, 2006, pages 319-325, vol. 47(3).
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Spine Solutions Brochure—Prodisc 2001, 16 pages.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4 ):571-7.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.
U.S. Appl. No. 60/424,055, filed Nov. 5, 2002, entitled Method and apparatus for spinal fixation.
U.S. Appl. No. 60/397,588, Method and apparatus for spinal fixation, filed Jul. 19, 2002.
U.S. Appl. No. 61/675,975, Expandable Implant, filed Jul. 26, 2012.
U.S. Appl. No. 60/942,998, Method and Apparatus for Spinal Stabilization, filed Jun. 8, 2007.
United States Disctrict Court, Central District of California, Case No. 1 :10-CV-00849-LPS, *Nuvasive, Inc.,* vs. *Globus Medical, Inc.,* Videotaped Deposition of: Luiz Pimenta, M.D., May 9, 2012, 20 pages.
U.S. Appl. No. 09/558,057, filed Apr. 26, 2000, entitled Bone Fixation System.
U.S. Appl. No. 14/640,220, filed Mar. 6, 2015, entitled Expandable Intervertebral Implant.
U.S. Appl. No. 14/685,358, filed Apr. 13, 2015, entitled Expandable Intervertebral Implant.
U.S. Appl. No. 14/685,402, filed Apr. 13, 2015, entitled Expandable Intervertebral Implant.

(56) References Cited

OTHER PUBLICATIONS

U.S. Appl. No. 60/794,171, filed Apr. 21, 2006, entitled Method and Apparatus for Spinal Fixation.
U.S. Appl. No. 62/950,180, filed Dec. 19, 2019, Spitler et al.
U.S. Appl. No. 60/557,246, filed Mar. 29, 2004 entitled: Device and Methods to Reduce and Stabilize Broken Bones.
Vandorpe, "Biodegradable Polyphosphazenes for Biomedical Applications", The Handbook of Biodegradable Polymers, edited by Domb et al., Hardwood Academic Press, 1997, pp. 161-182.
Vikram Talwar, "Insertion loads of the X Stop Interspinous Process Distraction System Designed to Treat Neurogenic Intermittent Claudication", Eur Spine J. (2006) 15: pp. 908-912.
Walsh et al., Preparation of porous composite implant materials by in situ polymerization of porous apatite containing epsilon-caprolactone or methyl methacrylate. Biomaterials. Jun. 2001; 22(11): 1205-12.
Zimmer.com, Longer BAK/L Sterile Interbody Fusion Devices. Date believed to be 1997. Product Data Sheet.Zimmer. Retrieved Jul. 23, 2012 from <http:/catalog.zimmer.com/contenUzpc/products/600/600/620/S20/S045.html>, 2 pages.
Zucherman, "A Multicenter, Prospective, Randomized Trial Evaluating the X Stop Interspinous Process Decompression System for the Treatment of Neurogenic Intermittent Claudication", Spine vol. 30, No. 12, pp. 1351-1358.

\* cited by examiner

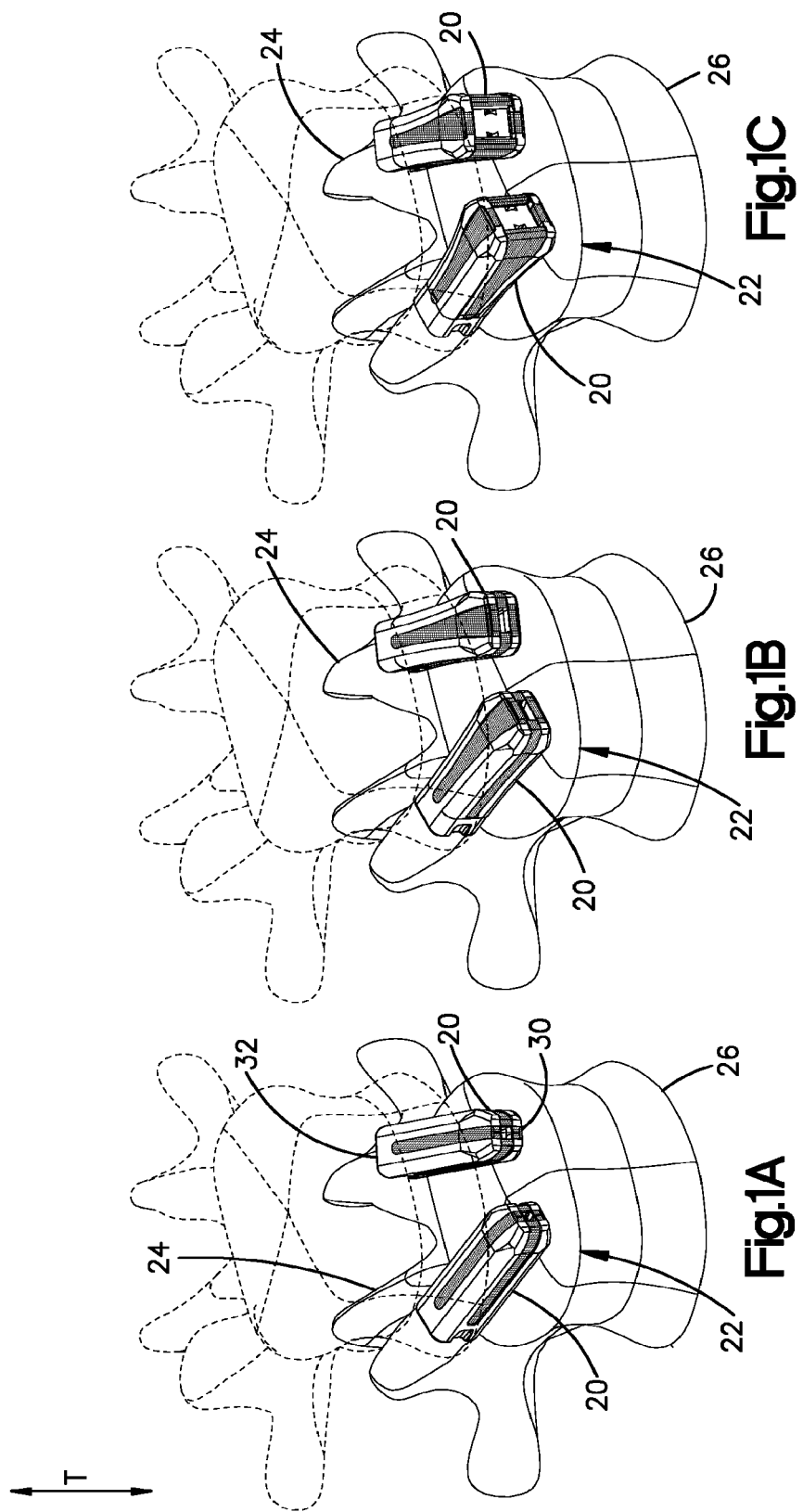

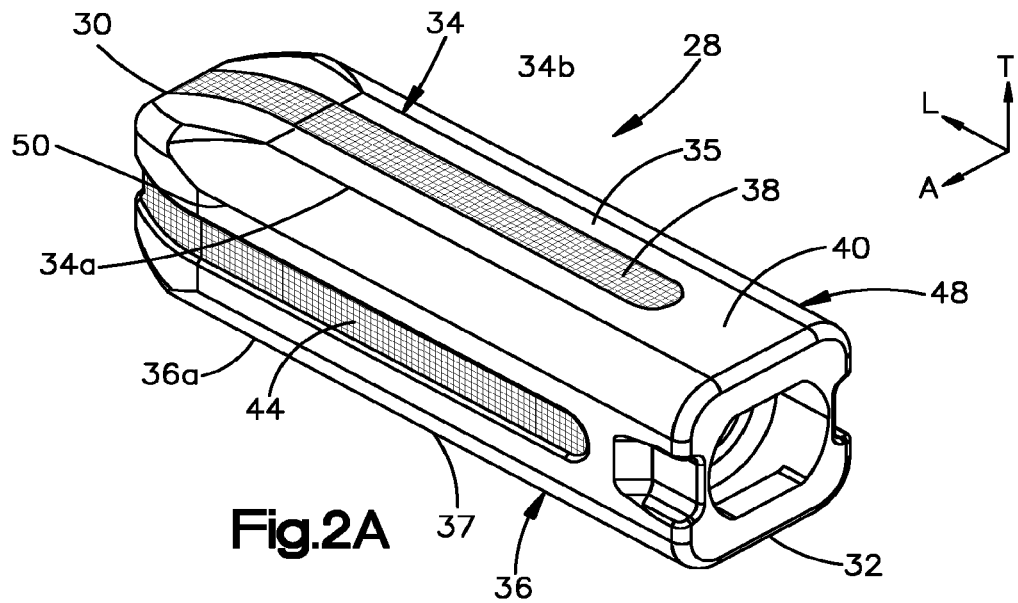
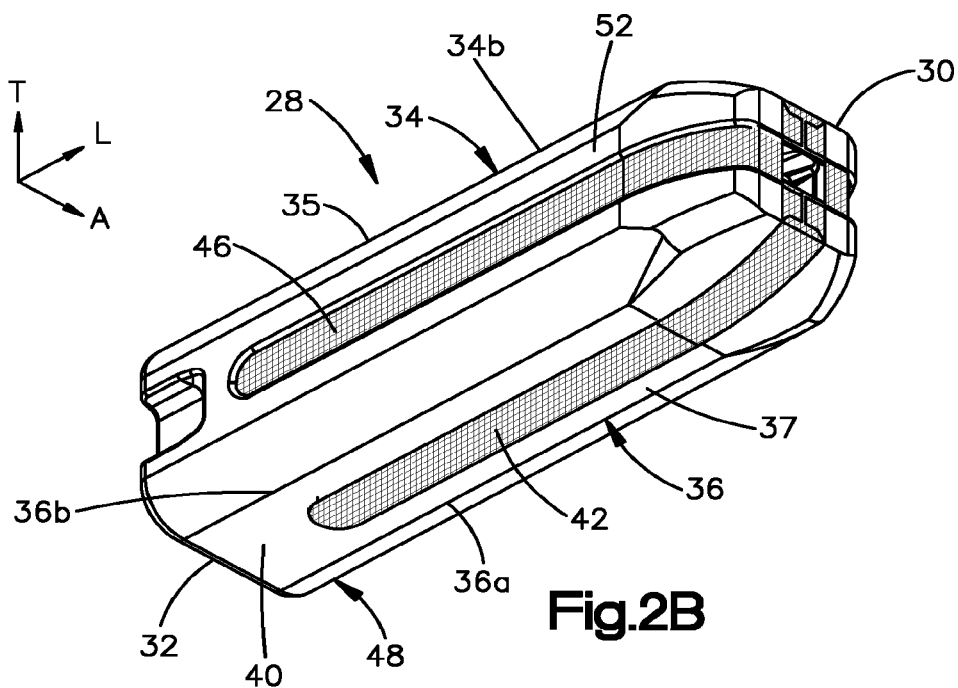

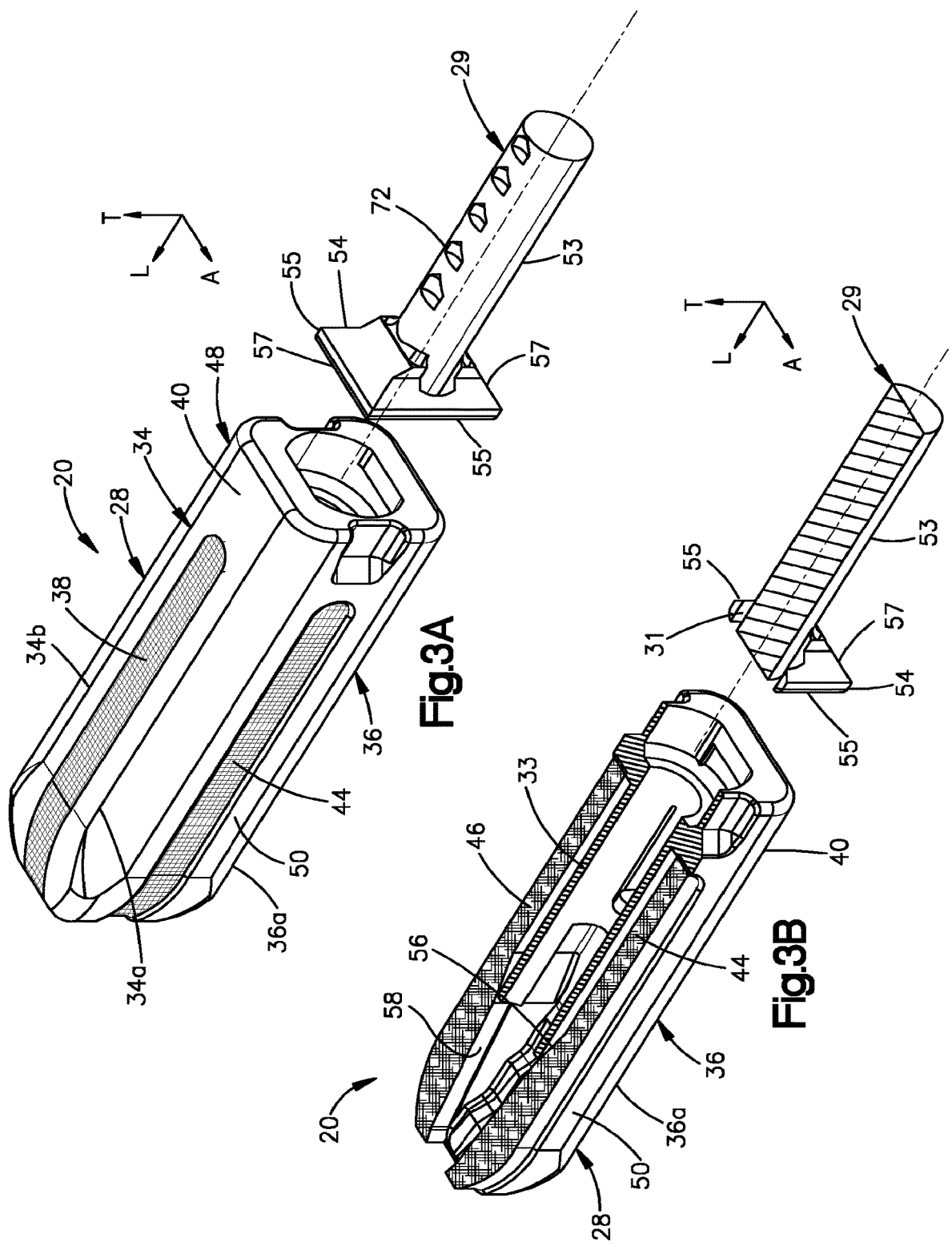

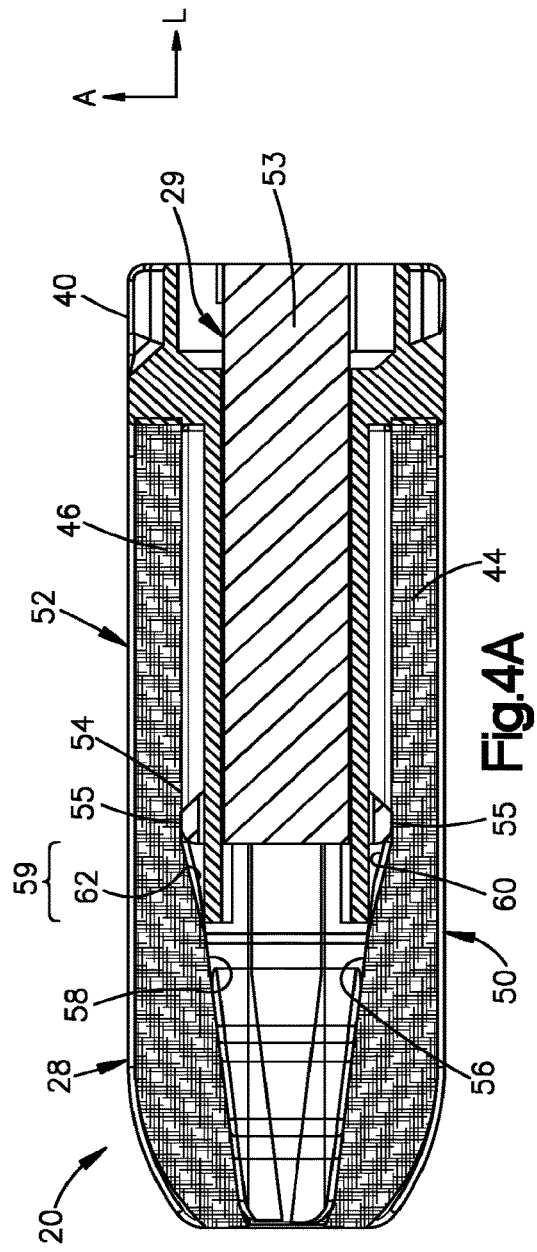
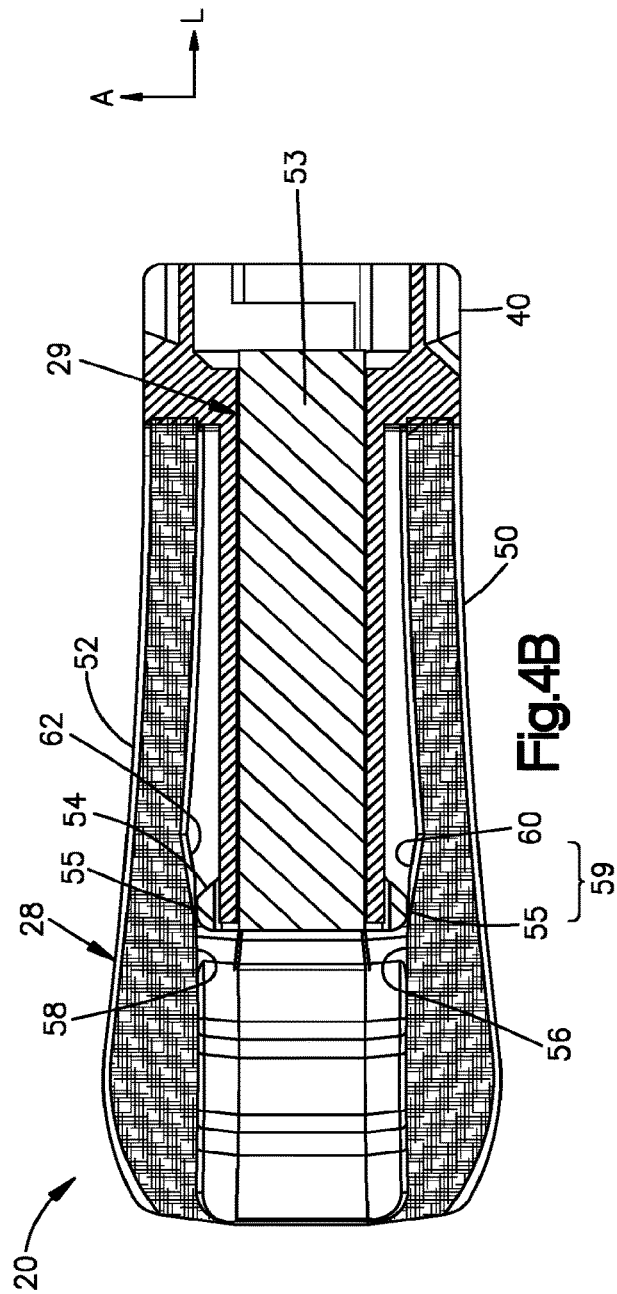

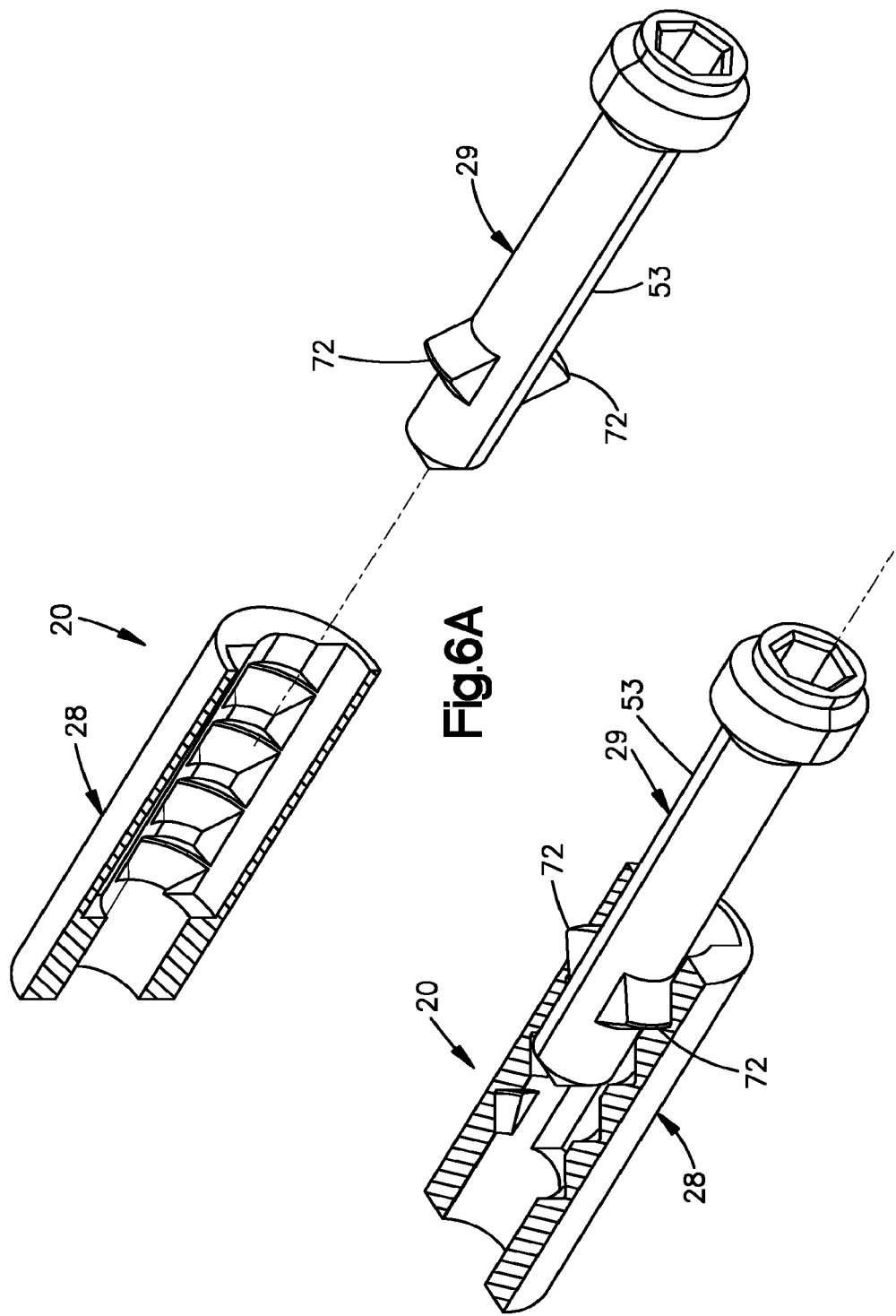

EXPANDABLE INTERVERTEBRAL IMPLANT

CROSS-REFERENCE TO RELATED APPLICATIONS

This is a continuation of U.S. patent application Ser. No. 16/842,058 filed Apr. 7, 2020, which claims priority to U.S. Patent Application Ser. No. 62/986,156 filed Mar. 6, 2020, the disclosure of which is hereby incorporated by reference as if set forth in its entirety herein.

BACKGROUND

1. Field

The present disclosure relates to orthopedic implantable devices, and more particularly implantable devices for stabilizing the spine. Even more particularly, the present disclosure is directed to expandable, angularly adjustable intervertebral cages comprising articulating mechanisms that allow expansion from a first, insertion configuration having a reduced size to a second, implanted configuration having an expanded size. The intervertebral cages are configured to adjust and adapt to lodortic angles, particularly larger lodortic angles, while restoring sagittal balance and alignment of the spine.

2. Description of the Related Art

The use of fusion-promoting interbody implantable devices, often referred to as cages or spacers, is well known as the standard of care for the treatment of certain spinal disorders or diseases. For example, in one type of spinal disorder, the intervertebral disc has deteriorated or become damaged due to acute injury or trauma, disc disease or simply the natural aging process. A healthy intervertebral disc serves to stabilize the spine and distribute forces between vertebrae, as well as cushion the vertebral bodies. A weakened or damaged disc therefore results in an imbalance of forces and instability of the spine, resulting in discomfort and pain. A typical treatment may involve surgical removal of a portion or all of the diseased or damaged intervertebral disc in a process known as a partial or total discectomy, respectively. The discectomy is often followed by the insertion of a cage or spacer to stabilize this weakened or damaged spinal region. This cage or spacer serves to reduce or inhibit mobility in the treated area, in order to avoid further progression of the damage and/or to reduce or alleviate pain caused by the damage or injury. Moreover, these type of cages or spacers serve as mechanical or structural scaffolds to restore and maintain normal disc height, and in some cases, can also promote bony fusion between the adjacent vertebrae.

However, one of the current challenges of these types of procedures is the very limited working space afforded the surgeon to manipulate and insert the cage into the intervertebral area to be treated. Access to the intervertebral space requires navigation around retracted adjacent vessels and tissues such as the aorta, vena cava, dura and nerve roots, leaving a very narrow pathway for access. The opening to the intradiscal space itself is also relatively small. Hence, there are physical limitations on the actual size of the cage that can be inserted without significantly disrupting the surrounding tissue or the vertebral bodies themselves.

Further complicating the issue is the fact that the vertebral bodies are not positioned parallel to one another in a normal spine. There is a natural curvature to the spine due to the angular relationship of the vertebral bodies relative to one another. The ideal cage must be able to accommodate this angular relationship of the vertebral bodies, or else the cage will not sit properly when inside the intervertebral space. An improperly fitted cage would either become dislodged or migrate out of position, and lose effectiveness over time, or worse, further damage the already weakened area.

Thus, it is desirable to provide intervertebral cages or spacers that not only have the mechanical strength or structural integrity to restore disc height or vertebral alignment to the spinal segment to be treated, but also be configured to easily pass through the narrow access pathway into the intervertebral space, and then accommodate the angular constraints of this space, particularly for larger lodortic angles.

SUMMARY

In one example, an intervertebral implant can include an implant body that defines a superior body configured to face a superior vertebra, and an inferior body configured to face an inferior vertebra. The implant can further include an actuator supported by the implant body, the actuator movable in the implant body from an initial position to a first expansion position, and subsequently from the first expansion position to a second expansion position. Movement of the actuator from the initial position to the first expansion position causes the actuator to urge the implant body to expand along a first direction of expansion, and movement of the actuator from the first expansion position to the second expansion position causes the actuator to urge the implant body to expand along a second direction of expansion that is perpendicular to the first direction of expansion.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 1A shows a pair of intervertebral implants inserted into an intervertebral space in a first insertion configuration;

FIG. 1B shows the intervertebral implants of FIG. 1A expanded along a first direction of expansion;

FIG. 1C shows the intervertebral implants of FIG. 1B further expanded along a second direction of expansion;

FIG. 2A is a first perspective view of an implant body of the pair of intervertebral implants illustrated in FIG. 1A;

FIG. 2B is a second perspective view of the implant body illustrated in FIG. 2A;

FIG. 3A is an exploded perspective view of an intervertebral implant of the pair of intervertebral implants illustrated in FIG. 1A;

FIG. 3B is a cross-sectional perspective view of the intervertebral implant illustrated in FIG. 3A;

FIG. 4A is a sectional side elevation view of the intervertebral implant illustrated in FIG. 3A, showing the implant in a first or initial configuration;

FIG. 4B is a sectional side elevation view of the intervertebral implant of FIG. 4A, but showing the implant expanded along a first direction of expansion;

FIG. 6A is an exploded perspective view of a portion of the intervertebral implant of FIG. 3A, showing a locking assembly constructed in accordance with one embodiment; and FIG. 6B is an exploded perspective view of the portion of the intervertebral implant of FIG. 6A, showing the locking assembly in a locked configuration.

DETAILED DESCRIPTION OF PREFERRED EMBODIMENTS

Figure 3C:
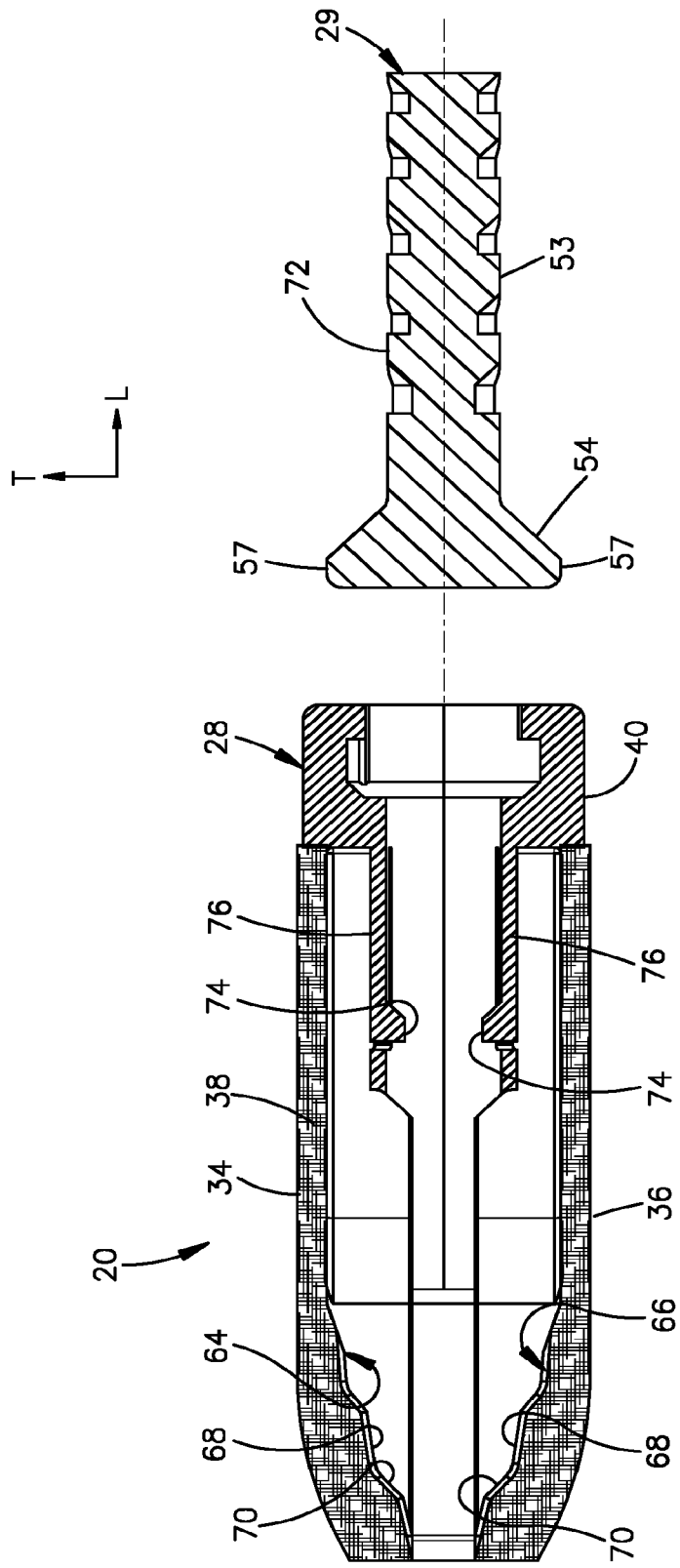
FIG. 3C is an exploded sectional side elevation view of the intervertebral implant illustrated in FIG. 3A.

The present disclosure provides various spinal or intervertebral implants, such as interbody fusion spacers, or cages, for insertion between adjacent vertebrae. The devices can be configured for use in either the cervical or lumbar region of the spine. In some embodiments, these devices are configured as PLIF cages, or posterior lumbar interbody fusion cages. These cages can restore and maintain intervertebral height of the spinal segment to be treated, and stabilize the spine by restoring sagittal balance and alignment. In some embodiments, the cages may contain an articulating mechanism to allow expansion and angular adjustment. This articulating mechanism allows upper and lower plate components to glide smoothly relative to one another.

As illustrated in FIG. 1A, one or more intervertebral implants 20 can be inserted into an intervertebral space 22 in a first, insertion configuration characterized by a first reduced size its insertion end to facilitate insertion through a narrow access passage. The one or more intervertebral implants 20 can be inserted in a PLIF approach into the intervertebral space. However, it is recognized that the one or more intervertebral implants 20 can be inserted along any suitable approach as desired. While a pair of intervertebral implants 20 are shown inserted into the intervertebral space, it is also appreciated that a single implant can be inserted into the intervertebral space having any suitable size and shape as desired. The intervertebral space 22 is defined by a superior vertebra 24 and an inferior vertebra 26 that are spaced from each other along a transverse direction T, which defines a cranial-caudal direction when the intervertebral implant 20 is disposed in the intervertebral space 22. As described herein, structure, elements, devices, and method steps described in the plural applies with equal force and effect to the singular unless otherwise indicated. For instance, while a pair of intervertebral implants 20 are illustrated as implanted in the intervertebral space 22 in FIG. 1A, it is appreciated that a single intervertebral implant 20 can alternatively be implanted in the intervertebral space 22. Conversely, as described herein, structure, elements, devices, and method steps described in the singular applies with equal force and effect to the plural unless otherwise indicated.

The intervertebral implants 20 may be inserted having the first reduced size as illustrated in FIG. 1A, and then expanded to a second, expanded configuration having an expanded size once implanted, as illustrated in FIGS. 1B and 1C. The second expanded size is greater than the first reduced size in at least one direction. In some embodiments, the second expanded size is greater than the first reduced size along two perpendicular directions that are each perpendicular to the direction of insertion. In their second expanded configuration, the cages are able to maintain the proper disc height and stabilize the spine by restoring sagittal balance and alignment.

For instance, as illustrated in FIG. 1B, the second expanded configuration can include a first expansion in a lateral direction A that is oriented perpendicular to the transverse direction T. In particular, the intervertebral implant 20 can expand in a first direction of expansion to achieve the first expansion along the lateral direction A. Thus, the first direction of expansion can be along the lateral direction A. That is, the implant has a first width along the lateral direction A in the first reduced size, and a second width along the lateral direction A in the second expanded size that is greater than the first width.

Further, as illustrated in FIG. 1C, the second expanded configuration can include a second expansion in a transverse direction T. In particular, the intervertebral implant 20 can expand in a second direction of expansion to achieve the second expansion along the transverse direction T. Thus, the second direction of expansion can be along the transverse direction T.

As described in more detail below, the intervertebral implant 20 can expand only along the first direction of expansion without expanding in the second direction of expansion. Subsequently, the intervertebral implant can expand only along the second direction of expansion without expanding in the first direction of expansion. In some examples, the implant can simultaneously expand along both the first and second directions of expansion after expanding only along the first direction of expansion and prior to expanding only along the second direction of expansion. Further, in some examples the intervertebral implant 20 can be expandable in the second direction of expansion only after expansion in the first direction of expansion has been completed.

It is contemplated that, in some embodiments, the intervertebral implant 20 may also be designed to expand in either or both of the first and second directions of expansion in a freely selectable (or stepless) manner to reach its second expanded configuration. The intervertebral implant 20 can further be configured to be able to adjust the angle of lordosis, and can accommodate larger lodortic angles in its second expanded configuration. Further, the intervertebral implant 20 may promote fusion to further enhance spine stability by immobilizing the adjacent vertebral bodies.

Additionally, the intervertebral implant 20 may be manufactured using selective laser melting (SLM) techniques, a form of additive manufacturing. The intervertebral implant 20 may also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral implant 20 disclosed herein can be formed of multiple, interconnected parts that do not require additional external fixation elements to keep together.

The intervertebral implant 20 manufactured in this manner does not have connection seams in some examples, whereas devices traditionally manufactured would have joined seams to connect one component to another. These connection seams can often represent weakened areas of traditionally manufactured implantable devices, particularly when the bonds of these seams wear or break over time with repeated use or under stress. By manufacturing the present intervertebral implant 20 using additive manufacturing, connection seams are avoided entirely and therefore the problem is avoided.

In addition, by manufacturing the intervertebral implant 20 using an additive manufacturing process, all of the components of the intervertebral implant 20 (including both an implant body and an actuator that is configured to expand the implant body as described below) remain a complete construct during both the insertion process as well as the expansion process. That is, multiple components of the intervertebral implant 20 are provided together as a collective single unit so that the collective single unit is inserted into the patient, actuated to allow expansion, and then allowed to remain as a collective single unit in situ. In contrast to other implantable implants requiring insertion of external screws or wedges for expansion, in the present embodiments the actuator does not need to be inserted into the cage, nor removed from the cage, at any stage during the process in some examples. This is because the actuator is manufactured to be captured internal to the implant body, and while freely movable within the cage, are already contained within the implant body so that no additional insertion or removal of the actuator is necessary.

In some embodiments, the implantable implant 20 can be made with a portion of, or entirely of, an engineered cellular structure that includes a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting to change the surface of the device on the nano level. One type of etching process may utilize, for example, HF acid treatment. In addition, these cages can also include internal imaging markers that allow the user to properly align the implantable implant 20 and generally facilitate insertion through visualization during navigation. The imaging marker shows up as a solid body amongst the mesh under x-ray, fluoroscopy or CT scan, for example.

Another benefit provided by the implantable implant 20 of the present disclosure is that they are able to be specifically customized to the patient's needs. Customization of the implantable implant 20 is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

Turning now to FIGS. 2A-3C, the intervertebral implant 20 includes an implant body 28 and an actuator 29 that is disposed in the implant body 28. The actuator 29 is configured to drive the implant body 28, and thus the intervertebral implant 20, to expand from the first insertion configuration to the second expanded configuration. The implant body 28, and thus the intervertebral implant 20, defines a distal end 30 and a proximal end 32 opposite the distal end 30. Thus, a distal direction is defined as a direction from the proximal end 32 toward the distal end 30. Conversely, a proximal direction is defined as a direction from the distal end toward the proximal end 32. The distal and proximal directions can be oriented along a longitudinal direction L. The longitudinal direction L can be perpendicular to each of the transverse direction T and the lateral direction A. The distal end 30 defines a leading end with respect to an insertion direction into the intervertebral space, and the proximal end 32 defines a trailing end with respect to the insertion direction into the intervertebral space.

Referring now in particular to FIGS. 2A-2B, the implant body 28 includes a superior body 34 and an inferior body 36 opposite the superior body 34 along the transverse direction T. The superior body 34 defines an exterior superior surface 35 that is configured to face and abut the superior vertebra 24, and the inferior body 36 defines an exterior inferior surface 37 that is configured to face and abut the inferior vertebra 26, respectively. In one example, the superior and inferior bodies 34 and 36 can define projections in the form of teeth, spikes, ridges, or the like, that are configured to grip the superior and inferior bodies 34 and 36 so as to limit or prevent migration of the intervertebral implant 20 in the intervertebral space.

The superior body 34 can be split into a first superior body portion 34a and a second superior body portion 34b. The first and second superior body portions 34a and 34b can be aligned with each other along the lateral direction A. Further, the first and second superior body portions 34a and 34b can be mirror images of each other. The implant body 28 can include an expandable superior mesh portion 38 that extends between the first superior body portion 34a and the second superior body portion 34b. For instance, the superior mesh portion 38 can extend from the first superior body portion 34a to the second superior body portion 34b. Thus, the superior mesh portion 38 couples the first superior body portion 34a to the second superior body portion 34b. The superior mesh portion 38 can extend to the distal end of the implant body 28, or can terminate at a location spaced in the proximal direction from the distal end of the implant body 28. The superior mesh portion 38 can be oriented along the lateral direction A. Therefore, as will be described in more detail below, the superior mesh portion 38 is expandable so as to permit one or both of the first and second superior body portions 34a and 34b to move away from the other of the first and second superior body portions 34a and 34b as the intervertebral implant 20 expands along the lateral direction A.

The implant body 28 can define a base 40 that is positioned such that the first and second superior body portions 34a and 34b extend in the distal direction from the base 40. The base 40 can define the proximal end 32 of the implant body 28, and can further define an aperture that is configured to receive an actuation tool that is configured to apply an actuation force to the actuator 29. The base 40 can be configured as an annular body that extends continuously about the perimeter of the implant body 28. Thus, in one example, the base 40 can lie in a plane that is oriented along the transverse direction T and the lateral direction A. When the intervertebral implant 20 is in the first insertion configuration, the first and second superior body portions 34a and 34b can extend parallel to each other. Further, the first and second superior body portions 34a and 34b can be spaced from each other by a first distance when the intervertebral implant 20 is in the first insertion configuration. Alternatively, the first and second superior body portions 34a and 34b can abut each other when the intervertebral implant 20 is in the first insertion configuration.

The inferior body 36 can be split into a first inferior body portion 36a and a second inferior body portion 36b. The first and second inferior body portions 36a and 36b can be aligned with each other along the lateral direction A. Further, the first and second inferior body portions 36a and 36b can be mirror images of each other. The first inferior body portion 36a can be aligned with the first superior body portion 34a along the transverse direction T. Similarly, the second inferior body portion 36b can be aligned with the second superior body portion 34b along the transverse direction T. The implant body 28 can include an expandable inferior mesh portion 42 that extends from the first inferior body portion 36a and the second inferior body portion 36b. For instance, the inferior mesh portion 42 can extend from the first inferior body portion 36a to the second inferior body portion 36b. Thus, the inferior mesh portion 42 couples the first superior body portion 34a to the second superior body portion 34b. The inferior mesh portion 42 can further extend in the distal direction from the base 40. The inferior mesh portion 42 can extend to the distal end of the implant body 28, or can terminate at a location spaced in the proximal direction from the distal end of the implant body 28. The inferior mesh portion 42 can be oriented along the lateral direction A. Therefore, as will be described in more detail below, the inferior mesh portion 42 is expandable so as to permit one or both of the first and second inferior body portions 36a and 36b to move away from the other of the first and second superior body portions 36a and 36b as the intervertebral implant 20 expands along the lateral direction A.

The first and second inferior body portions 36a and 36b can extend in the distal direction from the base 40. When the intervertebral implant 20 is in the first insertion configuration, the first and second inferior body portions 36a and 36b can extend parallel to each other. Further, the first and second inferior body portions 36a and 36b can be spaced from each other by a first distance when the intervertebral implant 20 is in the first insertion configuration. Alternatively, the first and second superior body portions 36a and 36b can abut each other when the intervertebral implant 20 is in the first insertion configuration.

The implant body 28 can further include an expandable first side mesh portion 44 that extends between the first superior body portion 34a to the first inferior body portion 36a. For instance, the first side mesh portion 44 can extend from the first superior body portion 34a to the first inferior body portion 36a. Thus, the first side mesh portion 44 couples the first superior body portion 34a to the first superior body portion 34a. The first side mesh portion 44 can further extend in the distal direction from the base 40. The first side mesh portion 44 can extend to the distal end of the implant body 28, or can terminate at a location spaced in the proximal direction from the distal end of the implant body 28. The first side mesh portion 44 can be oriented generally in the transverse direction T. Therefore, as will be described in more detail below, the first side mesh portion 44 is expandable along the transverse direction T so as to permit one or both of the first superior body portion 34a and the first inferior body portion 36a to move away from the other of the first superior body portion 34a and the first inferior body portion 36a as the intervertebral implant 20 expands along the transverse direction T.

The implant body 28 can further include an expandable second side mesh portion 46 that extends between the second superior body portion 34b to the second inferior body portion 36b. For instance, the second side mesh portion 46 can extend from the second superior body portion 34b to the second inferior body portion 36b. Thus, the second side mesh portion 46 couples the second superior body portion 34b to the second superior body portion 34b. The second side mesh portion 46 can further extend in the distal direction from the base 40. The second side mesh portion 46 can extend to the distal end of the implant body 28, or can terminate at a location spaced in the proximal direction from the distal end of the implant body 28. The second side mesh portion 46 can be oriented generally in the transverse direction T. Thus, as will be described in more detail below, the second side mesh portion 46 is expandable along the transverse direction so as to permit one or both of the second superior body portion 34b and the second inferior body portion 36b to move away from the other of the first superior body portion 34b and the first inferior body portion 36b as the intervertebral implant 20 expands along the transverse direction T.

In one example, the implant body 28 can be configured such that the base 40 in combination with the first and second superior body portions 34a-34b and the first and second inferior body portions 36a-36b define a frame 48. The implant body 28 can thus include the frame 48 and the mesh portions 38, 42, 44, and 46 that each can extend in the distal direction from the base 40. The first and second superior body portions 34a-34b and the first and second inferior body portions 36a-36b can be configured as arms that extend out from the frame 48 in the distal direction. Further, the first and second superior body portions 34a-34b and the first and second inferior body portions 36a-36b can define respective corners of an outer perimeter of the implant body in a plane that is oriented along each of the transverse direction T and the lateral direction A.

As shown, the first and second superior body portions 34a and 34b can be L-shaped in a plane that is oriented along the transverse direction T and the lateral direction A. That is, the first and second superior body portions 34a and 34b can each have a first region that extends laterally so as to define the exterior superior surface 35, and a second region that extends inferiorly toward the first and second inferior body portions 36a and 36b, respectively. Similarly, the first and second inferior body portions 36a and 36b can be L-shaped in the plane that is oriented along the transverse direction T and the lateral direction A. That is, the first and second inferior body portions 36a and 36b can each have a respective first region that extends laterally so as to define the exterior inferior surface 37, and a second region that extends superiorly toward the first and second superior body portions 36a and 36b, respectively.

Thus, the superior mesh portion 38 can extend from the first region of the first superior body portion 34a to the first region of the second superior body portion 34b. The inferior mesh portion can extend from the first region of the first inferior body portion 36a to the first region of the second inferior body portion 36b. The first side mesh portion 44 can extend from the second region of the first superior body portion 34a to the second region of the first inferior body portion 36a. The second side mesh portion 46 can extend from the second region of the second superior body portion 36a to the second region of the second inferior body portion 36b. It is recognized that any one or more up to all of the mesh portions can be interrupted by one or more additional superior body portions, inferior body portions, or side body portions.

The second regions of the first superior body portion 34a and the first inferior body portion 36a can define respective first and second portions of a first side wall 50 of the implant body 28. The second regions of the second superior body portion 34b and the second inferior body portion 36b can define respective first and second portions of a second side wall 52 of the implant body 28. Thus, the first and second portions of the first and second side walls 50 and 52, respectively are continuous with the first regions of the first and second superior body portions 34a and 34b, and the first and second inferior body portions 36a and 36b, respectively, along a respective plane that is oriented along the transverse direction T and the lateral direction A in one example. In other examples, the first and second portions of the first and second side walls 50 and 52, respectively, can be spaced from the first and second superior body portions 34a and 34b, and the first and second inferior body portions 36a and 36b, respectively, along the respective plane that is oriented along the transverse direction T and the lateral direction A.

The first and second superior body portions 34a and 34b and the first and second inferior body portions 36a and 36b can extend in the distal direction from the base 40. When the intervertebral implant 20 is in the first insertion configuration, the first and second inferior body portions 36a and 36b can extend parallel to each other. Further, the first and second inferior body portions 36a and 36b can be spaced from each other by a first distance when the intervertebral implant 20 is in the first insertion configuration. Alternatively, the first and second superior body portions 36a and 36b can abut each other when the intervertebral implant 20 is in the first insertion configuration. Similarly, the first superior body portion 34a and the first inferior body portion 36a can extend parallel to each other. Further, the first superior body portion 34a and the first inferior body portion 36a can be spaced from each other, for instance by the first distance, when the intervertebral implant 20 is in the first insertion configuration. Alternatively, the first superior body portion 34a and the first inferior body portion 36a can abut each other when the intervertebral implant 20 is in the first insertion configuration. Similarly still, the second superior body portion 34b and the second inferior body portion 36b can extend parallel to each other. Further, the second superior body portion 34b and the second inferior body portion 36b can be spaced from each other, for instance by the first distance, when the intervertebral implant 20 is in the first insertion configuration. Alternatively, the second superior body portion 34b and the second inferior body portion 36b can abut each other when the intervertebral implant 20 is in the first insertion configuration.

The distal end 30 of the implant body 28 can be tapered so as to facilitate insertion of the intervertebral implant 20 into the intervertebral space. That is, each of the first and second superior body portions 34a-34b and the first and second inferior body portions 36a and 36b can be tapered toward at least one or more up to all of the other of the first and second superior body portions 34a-34b and the first and second inferior body portions 36a and 36b at the distal end 30 of the implant body 28.

Referring now to FIGS. 3A-3C, the implant body 28 is configured to support the actuator 29 in an actuation cavity 50 of the implant body 28. In particular, the actuator 29 can be disposed in the actuation cavity 50 as-manufactured in an additive manufacturing process. Thus, the actuator 29 need not be separately inserted into the actuation cavity 50 in one example. Further, the actuator 29 can be dimensioned such that it is not able to be inserted into the actuation cavity. It should be appreciated, however, that the present disclosure is not limited to additively manufacturing the intervertebral implant 20 unless otherwise indicated.

The actuator 29 can include a shaft portion 53 and an enlarged head 54 that extends out from the shaft portion 53 along the transverse direction T and the lateral direction A. For instance, the enlarged head 54 can extend out from the shaft portion 53 along the transverse direction T both superiorly and inferiorly, and can further extend out from the shaft portion 53 in opposite lateral directions A. The enlarged head 54 defines first and second lateral expansion surfaces 55 and first and second transverse expansion surfaces 57. The enlarged head 54 can extend out from a distal terminal end of the shaft portion 53. The implant body 28 can guide the actuator 29 to translate along the longitudinal direction L in the actuation cavity upon application of an actuation force to the actuator 29 along the longitudinal direction L. For instance, the implant body 28 can include one or more guide arms 33 that are oriented along the longitudinal direction L and are received in a slot 31 of the actuator 29, thereby guiding the actuator 29 to translate along the longitudinal direction L. As will be described in more detail below, the enlarged head 54 is configured to urge the implant body 28 to expand along the first and second directions of expansion. While the enlarged head 54 defines the lateral and transverse expansion surfaces 55 and 57 in one example, it should be appreciated that any portion of the actuator 29 can alternatively define the lateral and transverse expansion surfaces 55 and 57, such as the shaft portion 53 of the actuator 29.

The implant body 28 can define first and second inner side surfaces 56 and 58 that are spaced from each other along the lateral direction A. The inner side surfaces 56 and 58 can be ramped so as to extend along the lateral direction A as they extend along the longitudinal direction L. That is, each of the first and second inner side surfaces 56 and 58 can include respective first and second ramped inner side surfaces 60 and 62 at a lateral expansion region 59 of the implant body 62. The first and second ramped side surfaces 60 and 62 each taper inward toward the other of the first and second inner side surfaces 56 and 58 as they extend in the distal direction. The first and second ramped side surfaces 60 can be mirror images of each other with respect to a midplane that is oriented along the longitudinal direction L and the transverse direction T. Thus, the first and second ramped side surfaces 60 and 62 can define equal and opposite slopes in one example. Further, the first and second ramped side surfaces 60 and 62 can be aligned with each other along the lateral direction A. Alternatively, the slopes of the first and second ramped side surfaces 60 and 62 can be different than each other. The first ramped side surface 60 can be defined by both the first superior body portion 34a and the first inferior body portion 36a. Similarly, the second ramped side surface 62 can be defined by both the second superior body portion 34b and the second inferior body portion 36b.

The implant body 28 can define an inner superior surface 64 and an inner inferior surface 66 that are spaced from each other along the transverse direction T. The inner superior surface 64 and the inner inferior surface 66 can be ramped along the transverse direction T as they extend along the longitudinal direction L at a transverse expansion region 61 of the implant body 28. That is, the inner superior surface 64 defines a superior ramped surface 65, and the inner inferior surface 66 defines an inferior ramped surface 67. The ramped surfaces 65 and 67 each taper inward toward the other of the inner superior surface 64 and the inner inferior surface 66 as they extend in the distal direction. The superior ramped surface 65 and the inferior ramped surface 67 can define equal and opposite slopes in one example. Alternatively, the slopes of the superior and inferior ramped surfaces 65 and 67 can be different than each other.

One or both of the ramped surfaces 65 and 67 can be stepped. Thus, the ramped surfaces 65 and 67 can include ramped surface segments 68 and risers 70 disposed between adjacent ramped surface segments 68. The risers 70 can have a slope greater than that of the ramped surface segments 68. Further, each of the risers 70 the superior ramped surface 65 can have the same slope, and each of the risers 70 of the inferior ramped surface 67 can have the same slope. The risers 70 of the superior ramped surface 65 and of the inferior ramped surface 67 can have the same slope as each other. The risers 70 can have a length along the longitudinal direction L that is less than the length of the ramped surface segments 68 along the longitudinal direction L.

The ramped surfaces 65 and 67 can be mirror images of each other about a midplane that is oriented along the longitudinal direction L and the lateral direction T. Thus, each of the ramped surface segments 68 of the superior ramped surface 65 can have the same slope, and each of the ramped surface segments 68 of the inferior ramped surface 67 can have the same slope. Further, the ramped surface segments 68 of the superior ramped surface 65 and the ramped surface segments 68 of the inferior ramped surface 67 can have the same slope as each other. The ramped surfaces 65 and 67 can be aligned with each other along the transverse direction T, such that the ramped surface segments 68 of the ramped surfaces 65 and 67 can be aligned with each other along the transverse direction T, and the risers 70 of the ramped surfaces 65 and 67 can be aligned with each other along the transverse direction T.

With continuing reference to FIG. 3C, the actuator 29 can define at least one actuator ratchet tooth 72 such as a plurality of actuator ratchet teeth 72. The actuator ratchet teeth 72 can be on one side of the actuator 29 or on opposed sides of the actuator 29. In one example, the actuator 29 includes first and second rows of actuator ratchet teeth 72 that are oriented along the longitudinal direction. The first and second rows of actuator ratchet teeth 72 can be opposite each other along the transverse direction T. Alternatively, the first and second rows of actuator ratchet teeth 72 can be opposite each other along the lateral direction A. Alternatively still, the actuator ratchet teeth 72 can have a length that extends about the actuator 29 a distance sufficient to define first and second portions at locations of the actuator 29 that are opposite each other. The actuator ratchet teeth 72 can be disposed on the shaft portion 53 of the actuator 29, but can be alternatively disposed as desired.

The implant body 28 can further define at least one implant ratchet tooth 74 that is configured to interlock with the at least one actuator ratchet tooth 72. The ratchet teeth 72 and 74 are configured to interlock so as to resist movement of the actuator 29 both in an expansion direction that causes the implant body 28 to iterate from the first insertion configuration toward the second expanded configuration, and in a contraction direction that causes the implant body to iterate from the second expanded configuration toward the first insertion configuration. In one example, the implant body 28 can include first and second rows of at least one implant ratchet tooth 74. The first and second rows of the at least one implant ratchet tooth can be aligned with the first and second rows of the at least one actuator tooth 72. Thus, the first and second rows of at least one implant ratchet tooth can interlock with first and second rows of at least one actuator ratchet tooth 72.

Further, the at least one actuator ratchet tooth 72 and the at least one implant ratchet tooth 74 can cam over each other as the actuator 29 is translated with respect to the implant body 28 along the longitudinal direction L. For instance, at least one or both of the at least one actuator ratchet tooth 72 and the at least one implant ratchet tooth 74 is displaceable away from the other of the at least one actuator ratchet tooth 72 and the at least one implant ratchet tooth 74.

In one example, the implant body 28 includes at least one flexible arm 76 that carries the at least one implant ratchet tooth 74. The at least one implant ratchet tooth 74 can be a single ratchet tooth 74 as illustrated, or a plurality of ratchet teeth 74. For instance, the implant body 28 includes first and second flexible arms 76 that each carry at least one implant ratchet tooth 74. Further, the at least one actuator tooth 72 is configured as a plurality of actuator teeth 72. As the actuator 29 is translated along the distal direction and the proximal direction, selectively, the at least one implant ratchet tooth cams 74 over the actuator teeth 72 as the flexible arm 76 resiliently deflects away from the actuator teeth 72. When the at least one implant ratchet tooth 74 is disposed between adjacent ones of the actuator teeth 72, the teeth 72 and 74 define a mechanical interference with each other to prevent inadvertent movement of the actuator 29. The mechanical interference can be overcome by application of an actuation force to the actuator 29 along the longitudinal direction. The actuator 29 can be guided to translate in the implant body 28 such that the actuator ratchet teeth 72 are aligned with the implant ratchet teeth 74 along the longitudinal direction L. That is, the implant body 28 can prevent the actuator 29 from rotating with respect to the implant body an amount that would bring the actuator teeth 72 out of longitudinal alignment with the implant ratchet teeth.

While each of the arms 76 carry a single implant ratchet tooth 74 and the actuator 29 carries a plurality of actuator ratchet teeth 72 in the illustrated example, other configurations are envisioned. For instance, each row of the implant body 28 can alternatively include a plurality of implant ratchet teeth 74 that are configured to intermesh with the at least one actuator ratchet tooth 72. Further, each row of the actuator 29 can include a single actuator ratchet tooth 72 or a plurality of actuator ratchet teeth 72. Further still, the actuator ratchet teeth 72 can be disposed on deflectable actuator arms if desired.

In still another example, referring to FIGS. 6A-6B, the actuator 29 can be rotatable about its central longitudinal axis. Thus, when the actuator is in a first rotational position, the actuator ratchet teeth 72 can be out of alignment with the implant ratchet teeth 74 with respect to the longitudinal direction L. Thus, the actuator 29 can be freely translatable in the implant body 28 along the longitudinal direction L without causing the actuator ratchet teeth 72 to mechanically interfere with the implant ratchet teeth 74. Once the actuator 29 has been translated to a desired longitudinal position, the actuator 29 can be rotated to a second rotational position, whereby the at least one implant ratchet tooth 74 is disposed between adjacent ones of the actuator ratchet teeth 72. In one example, the second rotational position can be ninety degrees offset from the first rotational position. Alternatively or additionally, the at least one actuator tooth 72 can be disposed between adjacent ones of a plurality of implant ratchet teeth 74. When the actuator 29 is in the second rotational position, mechanical interference defined by the ratchet teeth 72 and 74 prevent movement of the actuator 29 relative to the implant body 28 along the longitudinal direction L.

Figure 5A:
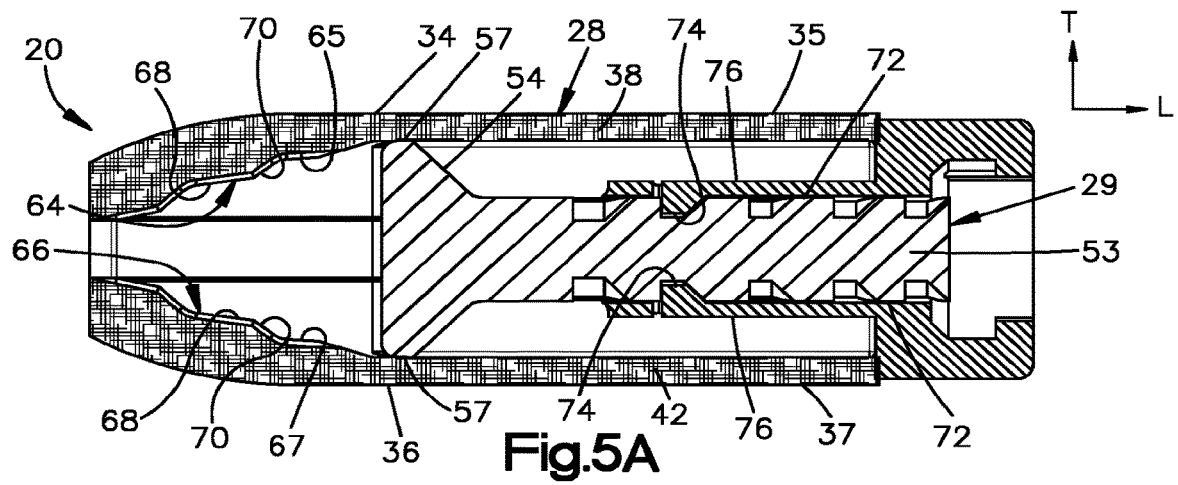
FIG. 5A is another sectional side elevation view of the intervertebral implant illustrated in FIG. 4B.
Figure 5B:
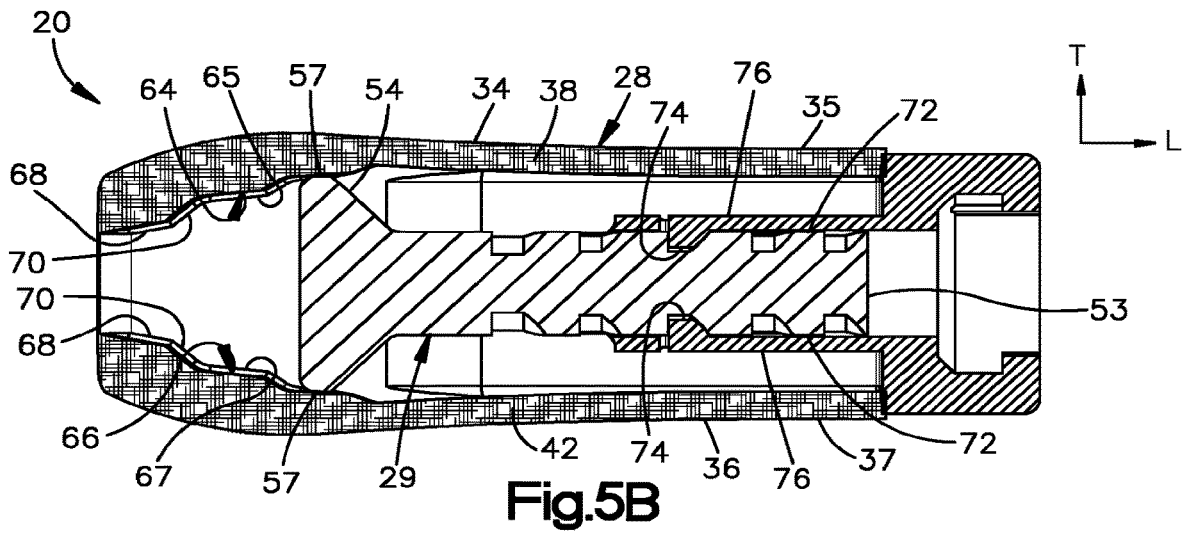
FIG. 5B is a side elevation view of the intervertebral implant illustrated in FIG. 5A, showing the implant expanded along a second direction of expansion.
Figure 5C:
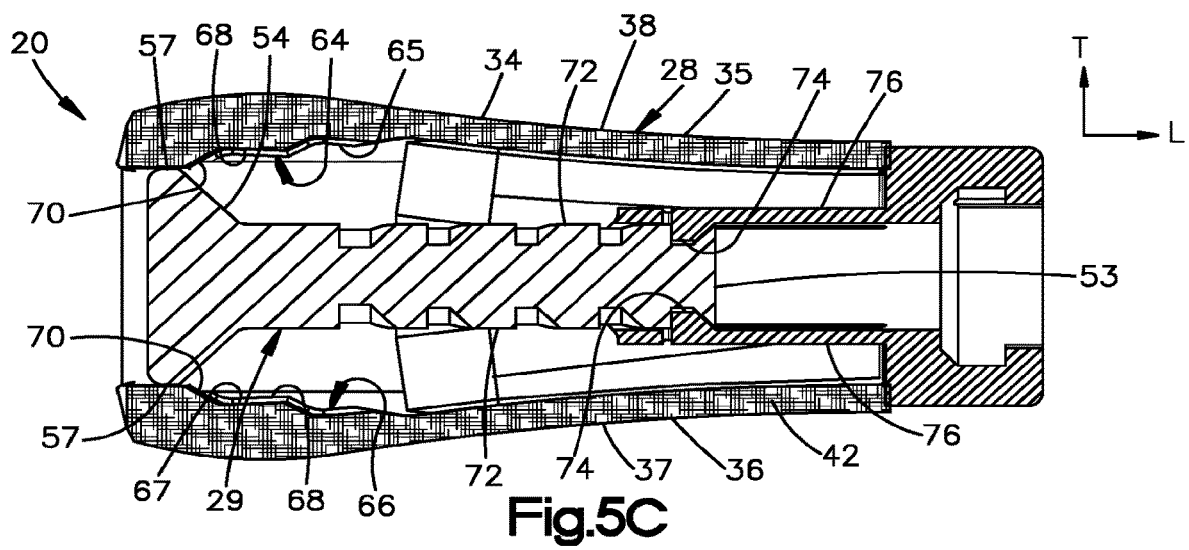
FIG. 5C is a side elevation view of the intervertebral implant illustrated in FIG. 5B, showing the implant further expanded along the second direction of expansion.

Referring now to FIGS. 4A-5C in general, operation of the intervertebral implant 20 will now be described. In particular, the actuator 29 is movable in the implant body 28 from an initial position shown in FIG. 4A to a first expansion position shown in FIG. 4B, and subsequently from the first expansion position to a second expansion position, shown in FIGS. 5B-5C. Movement of the actuator 29 from the initial position to the first expansion position causes the actuator 29 to urge the implant body 28 to expand along a first direction of expansion from the first configuration shown in FIG. 4A to the first expansion shown in FIG. 4B. Movement of the actuator 29 from the first expansion position to the second expansion position causes the actuator 29 to urge the implant body 28 to expand along the second direction of expansion that is perpendicular to the first direction of expansion, as illustrated in FIGS. 5B-5C. In one example, the actuator 29 is translatable in the distal direction from the initial position to the first expansion position, and further from the first expansion position to the second expansion position. For instance, the actuator 29 can translate in the distal direction without undergoing rotation. Alternatively, in an alternative example the actuator 29 can be configured as a screw that rotates as it translates in the distal direction.

Referring now to FIGS. 4A-4B in particular, when the actuator 29 is in the initial position, the implant body 28 is in the first or initial configuration. When the implant body 28 is in the first or initial configuration, the implant body 28 defines a first width along the lateral direction A and a first height along the transverse direction T. Further, when the actuator 29 is in the initial position, the enlarged head 54 can be spaced from the ramped side surfaces 60 and 62 in the proximal direction. Alternatively, the enlarged head 54 can be aligned with the ramped side surfaces 60 and 62 along the lateral direction A. Accordingly, when the actuator 29 is in the initial position, the actuator has not yet urged the implant body to expand along the first direction of expansion, which can be defined by the lateral direction A.

As the actuator 29 is translated in the distal direction from the first or initial position to the first expansion position in the lateral expansion region 59, the lateral expansion surfaces 55 ride along the first and second ramped side surfaces 60 and 62, thereby expanding the implant body 28 along the lateral direction A from the initial configuration to a laterally expanded configuration, which can define the first expansion. The implant body 28 defines a first lateral distance between the proximal ends of the ramped side surfaces 60 and 62 along the lateral direction A, and a second lateral distance between the distal ends of the ramped side surfaces that is less than the first lateral distance. Therefore, as the lateral expansion surfaces 55 ride along the first and second ramped side surfaces 60 and 62, the lateral expansion surface 55 urges the implant body 28 to expand along first direction of expansion to a second width along the lateral direction A that is greater than the first width. The first and second widths can be measured from the outer surface of the first side wall 50 to the outer surface of the second side wall 52.

In particular, each of the superior body 34 and the inferior body 36 can expand along the lateral direction A. For instance, the actuator 29 urges at least one or both of the first superior body portion 34a and the second superior body portion 34b (see FIG. 2A) away from the other of the first superior body portion 34a and the second superior body portion 34b along the lateral direction A. Further, the actuator 29 urges at least one or both of the first inferior body portion 36a and the second inferior body portion 36b (see FIG. 2B) away from the other of the first inferior body portion 36a and the second inferior body portion 36b along the lateral direction A. Further still, the actuator 29 can urge either or both of the first side wall 50 and the second side wall 52 away from the other of the first side wall 50 and the second side wall 52. The superior and inferior mesh portions 38 and 42 can expand along the lateral direction A as the implant body 28 expands along the lateral direction A.

While in one example the first and second inner side surfaces 56 and 58 are ramped, it should be appreciated that alternatively or additionally the lateral expansion surfaces 55 can be ramped. That is, the lateral expansion surfaces can be tapered toward each other along the lateral direction A as they extend in the distal direction. Thus, as the actuator 29 moves in the distal direction, the lateral expansion surfaces 55 can urge the implant body 28 to expand along the lateral direction A.

As described above, the first and second superior body portions 34a-34b and the first and second inferior body portions 36a-36b can each extend distally from the base 40. Thus, as the implant body 28 expands along the first direction of expansion, the first and second superior body portions 34a-34b and the first and second inferior body portions 36a-36b can flex laterally outward with respect to the base 40. Thus, the width of the implant body 28 along the lateral direction A at the proximal ends of the first and second superior body portions 34a-34b and the first and second inferior body portions 36a-36b can be less than the width of the implant body 28 along the lateral direction A at the distal ends of the first and second superior body portions 34a-34b and the first and second inferior body portions 36a-36b.

Referring now also to FIGS. 5A-5C, when the implant body 28 has expanded along the first direction of expansion, the actuator can be further translated along the distal direction from the first expansion position to the second expansion position, thereby expanding the implant to the second or expanded configuration. The second expansion position can be any position that causes the implant body 28 to expand along the second direction of expansion after expansion along the lateral direction A has completed. As will now be described, the second direction of expansion causes at least one or both of the superior and inferior bodies 34 and 36 to move away from the other of the superior and inferior bodies 34 and 36.

When the actuator 29 is in the first expansion position, the implant body 28 has a first height along the transverse direction T. The implant body 28 also has the first height when the actuator 29 is in the initial position and the implant body 28 is in the first or initial configuration. Further, when the actuator 29 is in the first expansion position, the enlarged head 54 can be spaced from the superior ramped surface 65 and the inferior ramped surface 67 along the proximal direction. Alternatively, the enlarged head 54 can be aligned with the superior and inferior ramped surfaces 65 and 67 along the transverse direction T. When the actuator 29 is in the first expansion position, the actuator 29 has not yet urged the implant body 28 to expand along the second direction of expansion, which can be defined by the transverse direction T.

As the actuator 29 is translated in the distal direction from the first expansion position toward the second expansion position, the transverse expansion surfaces 57 ride along the superior ramped surface 65 and the inferior ramped surface 67, thereby urging the implant body 28 to expand along the transverse direction T. The implant body 28 defines a first distance between the proximal ends of the superior and inferior ramped surfaces 65 and 67 along the transverse direction T, and a second transverse distance between the distal ends of the superior and inferior ramped surfaces 65 and 67 that is less than the first transverse distance. Therefore, as the transverse expansion surfaces 57 ride along the superior and inferior ramped surfaces 65 and 67, the transverse expansion surfaces 57 urge the implant body 28 to expand along the transverse direction A to a second height along the transverse direction T that is greater than the first height. In particular, the actuator 29 urges at least one or both of the superior body 34 and the inferior body 36 (see FIG. 2A) away from the other of the superior body 34 and the inferior body 36 along the transverse direction T. The first and second side mesh portions 44 and 46 can expand along the transverse direction as the implant body 28 expands along the transverse direction T. The mesh portions 38, 42, 44, and 46 can be constructed in accordance with any suitable embodiment as desired. In one example, the mesh portions can include a plurality of interconnected links that are movable with respect to each other so as to allow the mesh portions to expand along the respective directions.

As illustrated in FIG. 5C, when the implant 20 has been fully expanded along the second direction of expansion, the superior ramped surface 65 and the inferior ramped surface 67 can transition from the slopes described above to a second orientation that is less angled with respect to the longitudinal direction L. For instance, at least one or more of the superior and inferior ramped surfaces 65 and 67 can be oriented substantially along the longitudinal direction L, such as within +/−five degrees of the longitudinal direction L.

As described above, the superior and inferior bodies 34 and 36 can each extend distally from the base 40. Thus, as the implant body 28 expands along the second direction of expansion, the superior and inferior bodies 34 and 36 can flex outward with respect to the base 40 along the transverse direction T. Thus, the height of the implant body 28 along the transverse direction T at the proximal ends of the superior and inferior bodies 34 and 36 can be less than the height of the implant body 28 along the transverse direction T at the distal ends of the superior and inferior bodies 34 and 36. As a result, expansion of the implant body 28 along the second direction of expansion can change, for instance increase, a lordotic angle defined by the exterior superior surface 35 and the exterior inferior surface 37. Further expansion of the implant body 28 along the second direction of expansion can further change the lordotic angle.

As described above, the ramped surfaces 65 and 67 can include ramped surface segments 68 and risers 70 disposed between adjacent ramped surface segments 68. Thus, as the actuator 29 translates distally the transverse expansion surfaces 57 alternatingly ride along the ramped surface segments 68 and risers 70. The implant body 28 can achieve a fully expanded height when the actuator 29 has translated to a position whereby the actuator 29 can no longer be translated along the distal direction. Further as described above, the implant body 28 and the actuator 29 include respective ratchet teeth 72 and 74 that are configured to engage each other so as to lock the implant body 28 in the second or expanded position. When the ratchet teeth 72 and 74 engage each other, the actuator 29 can be prevented from translating in the proximal direction with respect to the implant body 28. In particular, at least one of the proximal surface of the implant ratchet teeth 74 and the distal surface of the actuator ratchet teeth 72 can be oriented to prevent the ratchet teeth 72 and 74 from camming over each other in the proximal direction. Thus, the actuator 29 can be prevented from translating in the proximal direction with respect to the implant body 28.

As a result, the actuator 29 can be translated in the distal direction to a position whereby the transverse expansion surfaces 57 are engaged with the respective ramped surfaces 65 and 67. The engagement of the ratchet teeth 72 and 74 can prevent the actuator 29 from translating in the proximal direction, which would cause the implant to collapse along the transverse direction T. Thus, the implant can be expanded to a position to a height along the transverse direction T that is less than the fully expanded height. Further, the ratchet teeth 72 and 74 can engage when the actuator 29 is in the first expansion position. Thus, the implant 28 can be locked in the laterally expanded configuration so as to prevent contraction of the implant 28 along the lateral direction A without expanding along the transverse direction T. Further, the implant 28 can be locked in the laterally expanded configuration and in a transverse expanded configuration having an expanded height less than the fully expanded height. Accordingly, expansion of the implant 20 along the transverse direction T can be controlled after the implant 20 has been fully expanded along the lateral direction A.

The first and second inner side surfaces 56 and 58 at the transverse expansion region 61 can be oriented along respective planes that are defined by the transverse direction T and the longitudinal direction L when the implant 20 has achieved the first expansion. Thus, as the lateral expansion surfaces 55 ride along the first and second inner side surfaces 56 and 58 as the actuator translates in the distal translation of the actuator 29 in the transverse expansion region 61, the lateral expansion surfaces 55 do not urge the implant body 28 to expand along the lateral direction A. Accordingly, distal translation of the actuator head 54 in the transverse expansion region 61 causes the implant to expand along the transverse direction T without expanding along the lateral direction A. Alternatively, the first and second inner side surfaces 56 and 68 can be sloped inwardly toward each other along the lateral direction A as they extend in the distal direction. Thus, distal translation of the actuator 29 in the transverse expansion region 61 can cause the lateral expansion surfaces 55 of the actuator 29 urge the implant body 28 to further expand along the lateral direction A. In one example, the slope of the first and second inner side surfaces 56 and 68 can be less than the slope of the ramped inner side surfaces 60 and 62.

While in one example the superior and inferior surfaces 64 and 66, respectively, are ramped, it should be appreciated that alternatively or additionally the transverse expansion surfaces 57 can be ramped. That is, transverse expansion surfaces 57 can be tapered toward each other along the transverse direction T as they extend in the distal direction. Thus, as the actuator 29 moves in the distal direction, the transverse expansion surfaces 57 can urge the implant body 28 to expand along the lateral direction T.

As described above, at least a portion up to an entirety of the transverse expansion region 61 can be disposed distal of the lateral expansion region 59. Thus, at least respective portions up to respective entireties of the superior and inferior ramped surfaces 65 and 67 can be disposed distal of the ramped side surfaces 60 and 62. Accordingly, in one example, movement of the actuator 29 from the initial position to the first expansion position does not urge the implant body 28 to expand along the second direction of expansion. Alternatively, a portion of the vertical expansion region 61 can partially overlap the lateral expansion region 59. Accordingly, the implant body 28 can further expand along the lateral direction A as it expands along the transverse direction T. In both examples, at least a portion of the vertical expansion region 61 extends distal of the lateral expansion region 59, and the implant is expandable along the transverse direction T without expanding along the lateral direction A.

As described above, the first direction of expansion can be along the lateral direction A, and the second direction of expansion can be along the transverse direction T. Alternatively, the first direction of expansion can be along the transverse direction T, and the second direction of expansion can be along the lateral direction A. In this regard, at least a portion of the lateral expansion region 59 can be disposed distal of the transverse expansion region 61.

It should be appreciated that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should be further appreciated that the various alternative embodiments described above with respect to one illustrated embodiment can apply to all embodiments as described herein, unless otherwise indicated.

What is claimed is:

1. A method for implanting an intervertebral implant, the method comprising the steps of:
    inserting the intervertebral implant into an intervertebral space, such that a superior body of the intervertebral endplate faces a superior vertebra, and an inferior body of the intervertebral implant faces an inferior vertebra;
    moving an actuator of the implant from an initial position to a first expansion position, such that the actuator urges the implant body to expand along a first direction of expansion without urging the implant body to expand along a second direction of expansion that is perpendicular to the first direction; and
    subsequently moving the actuator from the first expansion position to a second expansion position, such that the actuator urges the implant body to expand along the second direction of expansion.

2. The method of claim 1, wherein the moving and subsequently moving steps are in a distal direction.

3. The method of claim 2, wherein the first direction of expansion is perpendicular to the distal direction, and the second direction of expansion is perpendicular to the distal direction and the first direction.

4. The method of claim 1, wherein the moving and subsequently moving steps comprise causing a head of the actuator to urge the implant body to expand along the first and second directions of expansion, respectively.

5. The method of claim 1, wherein the subsequently moving steps does not cause the actuator to urge the implant body to expand along the first direction of expansion.

6. The method of claim 1, wherein the moving step causes each of the superior body and the inferior body to laterally expand, and the subsequently moving step causes at least one of the superior and inferior bodies to move away from the other of the superior and inferior bodies along a vertical direction.

7. The method of claim 1, wherein the moving step comprises engaging the actuator with opposed ramped inner side surfaces of the implant, and the subsequently moving step comprises engaging the actuator with opposed ramped superior and inferior surfaces that are spaced distally from the ramped inner side surfaces, and the moving and subsequently moving steps comprise moving the actuator distally.

8. The method of claim 7, wherein the ramped inner superior and inferior surfaces are stepped.

9. The method of claim 7, wherein the actuator comprises a shaft portion and an enlarged head that extends out from the shaft portion along both the first and second directions of expansion, and the moving and subsequently moving steps comprise causing the enlarged head to urge the implant body to expand along the first and second directions of expansion.

10. The method of claim 1, wherein the subsequently moving step comprises changing a lordotic angle defined by an exterior superior surface of the superior body and an external inferior surface of the inferior body.

11. The method of claim 10, wherein the subsequently moving step comprises increasing the lordotic angle.

12. The method of claim 1, wherein the implant body comprises a frame that includes a base and each of the superior and inferior bodies that extends distally from the base.

13. The method of claim 12, wherein the subsequently moving step comprises causing the superior and inferior bodies to flex about the base as the implant body expands along the second direction of expansion.

14. The method of claim 1, wherein 1) the superior body comprises a first superior body portion, a second superior body portion, and a superior expandable mesh that couples the first superior body portion to the second superior body portion, and 2) the inferior body portion comprises a first inferior body portion, a second inferior body portion, and an inferior expandable mesh that couples the first inferior body portion to the second inferior body portion.

15. The method of claim 1, wherein the moving step comprises 1) causing at least one of the first and second superior body portions to move away from the other of the first and second superior body portions, and 2) causing at least one of the first and second inferior body portions to move away from the other of the first and second inferior body portions.

16. The method of claim 15, wherein the moving step comprises expanding a superior mesh that extends between the first and second superior body portions, and expanding an inferior mesh that extends between the first and second inferior body portions.

17. The method of claim 16, wherein the subsequently moving step comprises expanding a first side mesh that couples the first superior body portion to the first inferior body portion, and expanding a second side mesh that couples the second superior body portion to the second inferior body portion.

* * * * *